US012409244B2

(12) United States Patent
Batts

(10) Patent No.: US 12,409,244 B2
(45) Date of Patent: Sep. 9, 2025

(54) HANDHELD BLOWER DEVICES, SYSTEMS, AND COMPONENTS, AND RELATED METHODS

(71) Applicant: Felix Batts, Raleigh, NC (US)

(72) Inventor: Felix Batts, Raleigh, NC (US)

( * ) Notice: Subject to any disclaimer, the term of this patent is extended or adjusted under 35 U.S.C. 154(b) by 476 days.

(21) Appl. No.: 18/101,759

(22) Filed: Jan. 26, 2023

(65) Prior Publication Data

US 2023/0241271 A1 Aug. 3, 2023

Related U.S. Application Data

(60) Provisional application No. 63/303,057, filed on Jan. 26, 2022.

(51) Int. Cl.
| | |
|---|---|
| *A61L 2/22* | (2006.01) |
| *A61L 2/26* | (2006.01) |
| *A61L 9/20* | (2006.01) |
| *F04D 19/00* | (2006.01) |
| *F04D 25/06* | (2006.01) |
| *F04D 29/58* | (2006.01) |
| *F04D 29/70* | (2006.01) |

(52) U.S. Cl.

CPC .................................... *A61L 2/22* (2013.01); *A61L 2/26* (2013.01); *A61L 9/20* (2013.01); *F04D 19/002* (2013.01); *F04D 25/06* (2013.01); *F04D 29/582* (2013.01); *F04D 29/701* (2013.01); *A61L 2202/11* (2013.01); *A61L 2202/15* (2013.01); *A61L 2202/16* (2013.01); *A61L 2209/12* (2013.01)

(58) Field of Classification Search
CPC ..... A61L 2/22; A61L 2/26; A61L 9/20; F04D 19/002; F04D 25/06; F04D 29/582; F04D 29/701

See application file for complete search history.

(56) References Cited

U.S. PATENT DOCUMENTS

| | | | | | |
|---|---|---|---|---|---|
| 8,025,243 | B2 | 9/2011 | Charpie | | |
| 10,894,262 | B1 | 1/2021 | Cooper | | |
| 10,926,275 | B1 | 2/2021 | Kinne et al. | | |
| 2005/0196158 | A1 * | 9/2005 | Semaza | F04D 29/388 | 392/362 |
| 2009/0310949 | A1 * | 12/2009 | Collier | F28D 15/00 | 165/104.19 |
| 2019/0060922 | A1 | 2/2019 | Wright | | |
| 2020/0121867 | A1 | 4/2020 | Wright | | |

FOREIGN PATENT DOCUMENTS

| | | | | |
|---|---|---|---|---|
| EP | 2234730 A1 | | 10/2010 | |
| GB | 2172935 A | * | 10/1986 | H01R 39/08 |
| WO | 2009079280 A1 | | 6/2009 | |
| WO | 2012150614 A1 | | 11/2012 | |

* cited by examiner

*Primary Examiner* — Sean E Conley
(74) *Attorney, Agent, or Firm* — The Law Firm of Andrea Hence Evans, LLC

(57) ABSTRACT

Handheld devices and systems for effectively spraying an area, and improved components for these and other devices and systems. A handheld air blower device includes heated fan blade components, which may be integrated or modular with the device, and which are configured to heat substances being sprayed with the device to improve operation of the device. The handheld air blower device may be used to spray disinfectant compositions to disinfect the area.

22 Claims, 26 Drawing Sheets

HANDHELD BLOWER DEVICES, SYSTEMS, AND COMPONENTS, AND RELATED METHODS

CROSS-REFERENCE TO RELATED APPLICATIONS

This application claims priority to U.S. Provisional Application No. 63/303,057 filed Jan. 26, 2022.

STATEMENT REGARDING FEDERALLY SPONSORED RESEARCH OR DEVELOPMENT

None.

FIELD

The disclosure relates to handheld devices and systems for effectively spraying an area, and improved components for these and other devices and systems. A handheld air blower device includes heated fan blade components, which may be integrated or modular with the device, and which are configured to heat substances being sprayed with the device to improve operation of the device. The handheld air blower device may be used to spray disinfectant compositions to disinfect the area.

BACKGROUND

There are many scenarios in which a large area must be efficiently and effectively disinfected within a short period of time. Containment protocols for managing biological substances may require prompt disinfection of an area after a breach or outbreak of a biological substance from a controlled setting. Existing approaches to disinfect areas may not be suitably efficient or effective.

Accordingly, there is a need for improved handheld devices and systems for effectively spraying an area with a composition, such as a disinfectant composition. The present invention addresses this unmet need.

SUMMARY

In general, the disclosure provides improved handheld blower devices having improved heatable fan blade components which may be modularly or integrally installed therein. The handheld blower device is configured for improved performance compared to previous iterations and provides more effective coverage of an area with a solution sprayed therefrom. The heatable fan blade components may improve operation of the handheld blower devices by heating an air column within the device, heating the solution, and/or heating an aerosolized form of the solution prior to ejection from a spray nozzle of the device. An improved handheld blower device (e.g., a Mini-E™ device as provided by Advanced Non-Lethal Technologies Inc. of North Carolina, United States) may include a handheld axial air blower capable of spraying a plurality of liquid-coatings, e.g., disinfectant compositions, to cover large areas with speed and efficiency. The device includes spray nozzles, positioned at a top and a bottom of the device, configured to deliver the solution as a fine mist or aerosol that is directed and controlled by the axial air blower. With the combination of the axial air blower and spray nozzles, an operator assumes full command, ensuring improved surface coverage.

In one aspect, the disclosure provides a heatable fan blade component for a handheld blower device, the heatable fan blade component comprising a fan blade having a resistor puck disposed within a cavity of the fan blade. When a current passes through the resistor puck, the resistor puck and the cavity are heated. The current may be deliverable by a power source, internal or external to the device, that is operably connectable to the resistor puck and configurable to deliver the current thereto. In various implementations, the power source includes a brushless direct current (BLDC) motor that may include a stator and a receiver coil operably connected to the resistor puck, such that the stator is configured to produce an alternating magnetic field to transfer the current to the receiver coil and the resistor puck.

In another aspect, the disclosure provides a handheld blower device, comprising a heatable fan blade component comprising a fan blade having a resistor puck disposed within a cavity of the fan blade. When a current passes through the resistor puck, the resistor puck and the cavity are heated. The device includes or is operably connectable to a power source configured to connect to the resistor puck and deliver the current thereto. In various implementations, the power source includes a brushless direct current (BLDC) motor that may include a stator and a receiver coil operably connected to the resistor puck, such that the stator is configured to produce an alternating magnetic field to transfer the current to the receiver coil and the resistor puck.

In yet another aspect, the disclosure provides methods of assembly and use of the heatable fan blade component and the handheld blower device. A method for spraying a solution onto an area with a handheld blower device comprises filling a solution bottle of the handheld blower device with the solution; configuring a spray nozzle of the handheld blower device for use; activating a pump of the handheld blower device to pump the solution from the solution bottle to the spray nozzle; actuating a trigger of the handheld blower device to activate an axial blower fan of the handheld blower device; and directing the spray nozzle of the handheld blower device toward the area to spray the solution from the spray nozzle onto the area. In various implementations of the method, the handheld blower device comprises a heatable fan blade component comprising a fan blade having a resistor puck disposed within a cavity of the fan blade, such that when a current passes through the resistor puck, the resistor puck and the cavity are heated; and a power source is operably connected to the resistor puck and configured to deliver the current thereto. In various implementations, the power source includes a brushless direct current (BLDC) motor that may include a stator and a receiver coil operably connected to the resistor puck, such that the stator is configured to produce an alternating magnetic field to transfer the current to the receiver coil and the resistor puck.

The invention generally relates to heatable fan blade components and handheld blower devices which may be manufactured with appropriate materials and processes and which may be scaled as needed.

Other objects, features, and advantages of the invention will become apparent from the following detailed description taken in conjunction with the accompanying drawings.

BRIEF DESCRIPTION OF THE DRAWINGS

Although the characteristic features of the invention will be particularly pointed out in the claims, the invention itself and manners in which it may be made and used may be better understood after a review of the following description, taken in connection with the accompanying drawings, wherein like numeral annotations are provided throughout.

Figure 5:
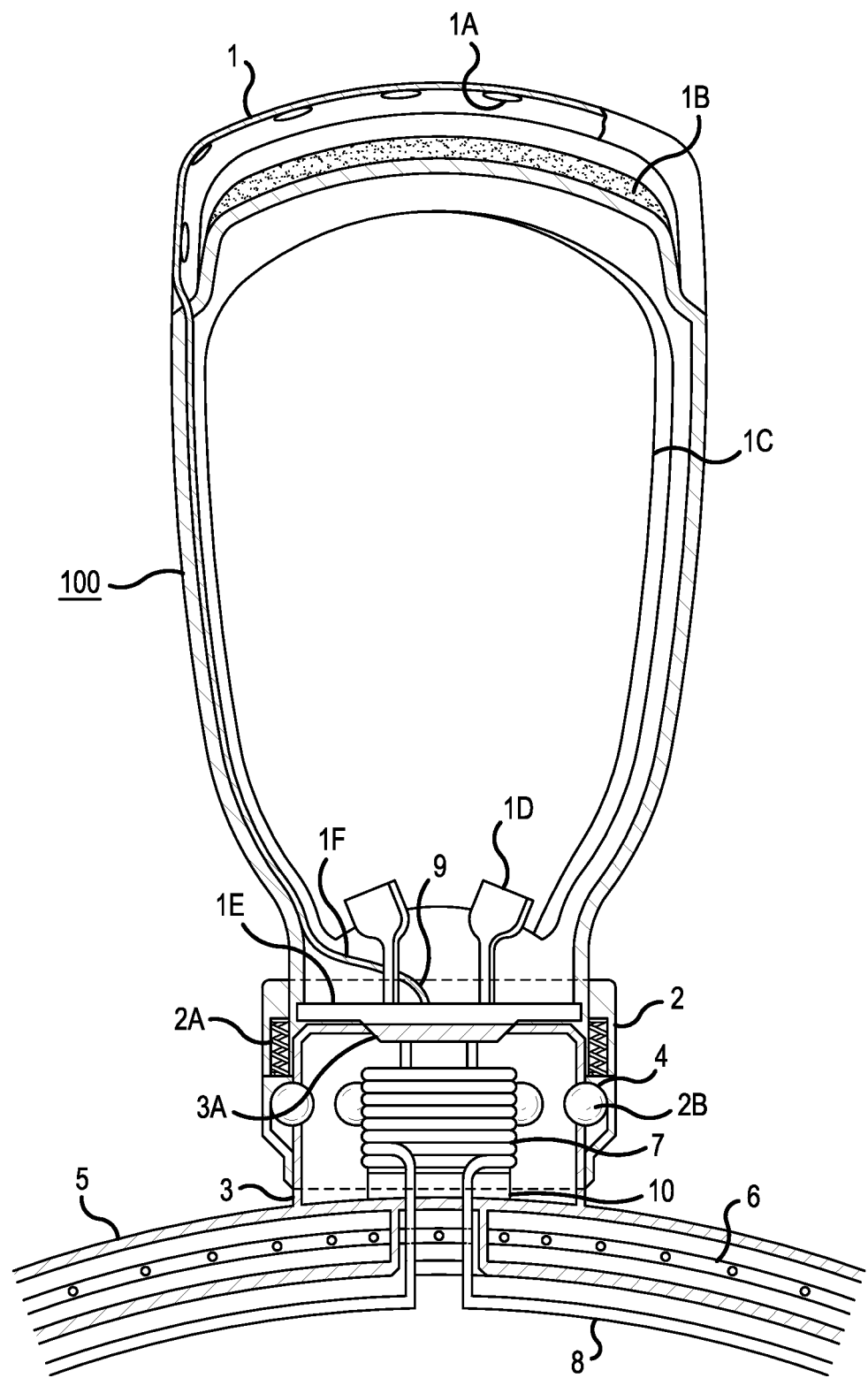

FIG. 5 depicts a cross-section-view of the modular heatable fan blade with closures of the internal structure and other components. The modular heatable fan blade is heated through an electrical resistive mechanic mechanism whereby electricity passes through a resistive material and the atomic structure of the material slows propagation of the electron flow, creating friction which results in heat. For the shown embodiment, the modular heatable fan blade is shown coupled with the low-profile coupling hub of the unit.

FIGS. 6A, 6B, 6C, 6D, 6E, 6F, 6G, and 6H depicts views of an exemplary handheld blower device having four spray nozzles and their components.

Figure 7:
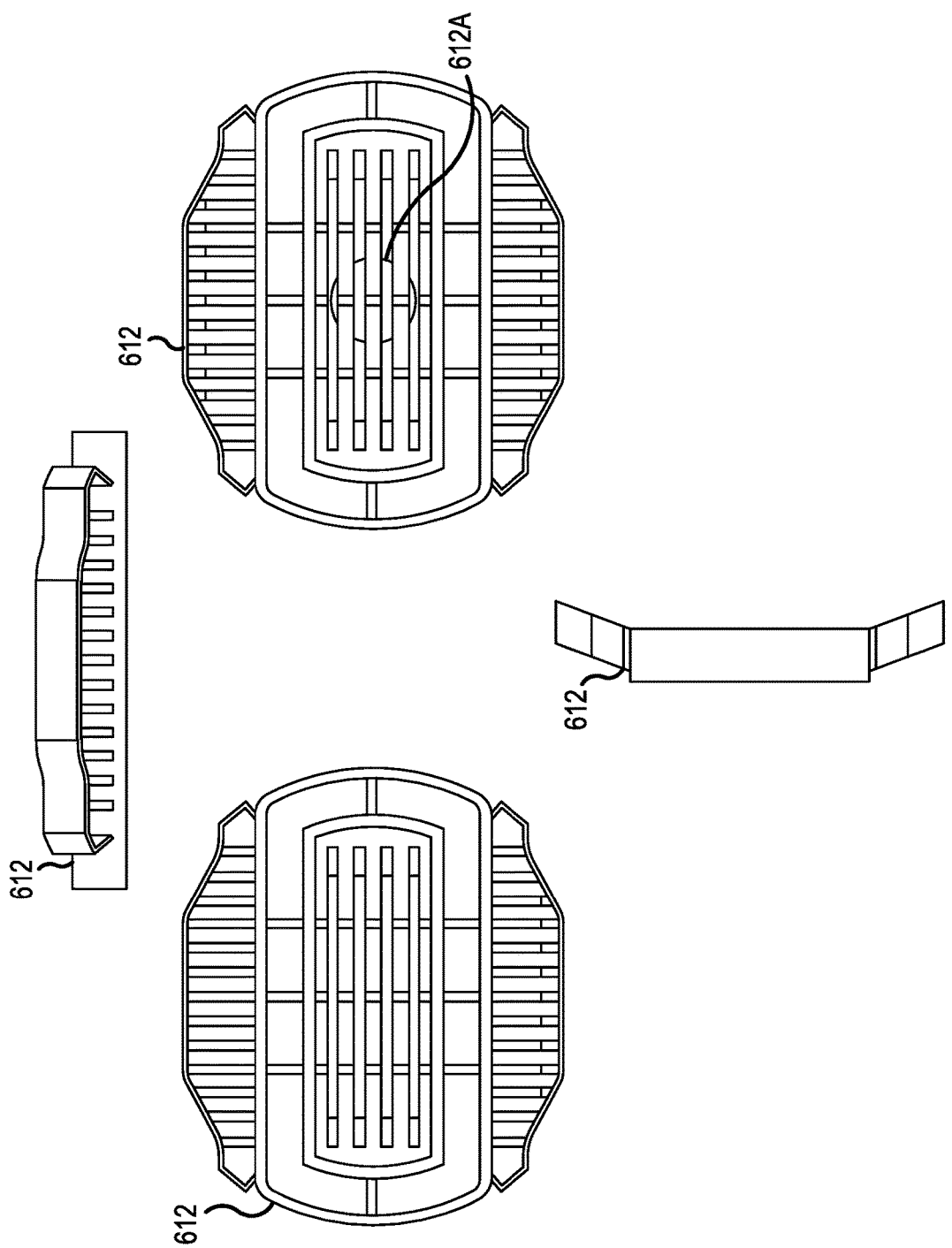

FIG. 7 depicts an exemplary component of an exemplary handheld blower device having four spray nozzles relating to a finger guard.

Figure 8A:
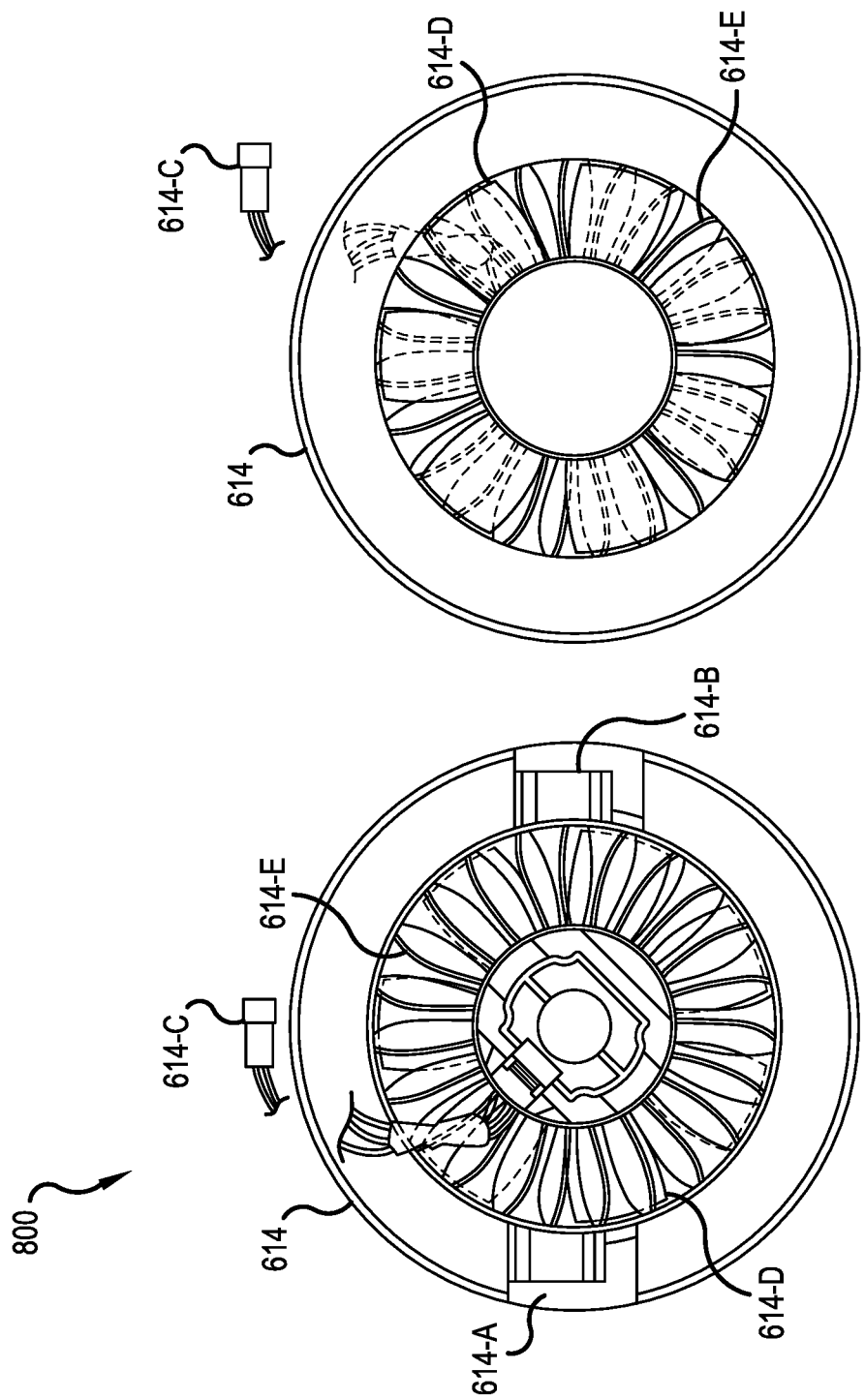
Figure 8B:
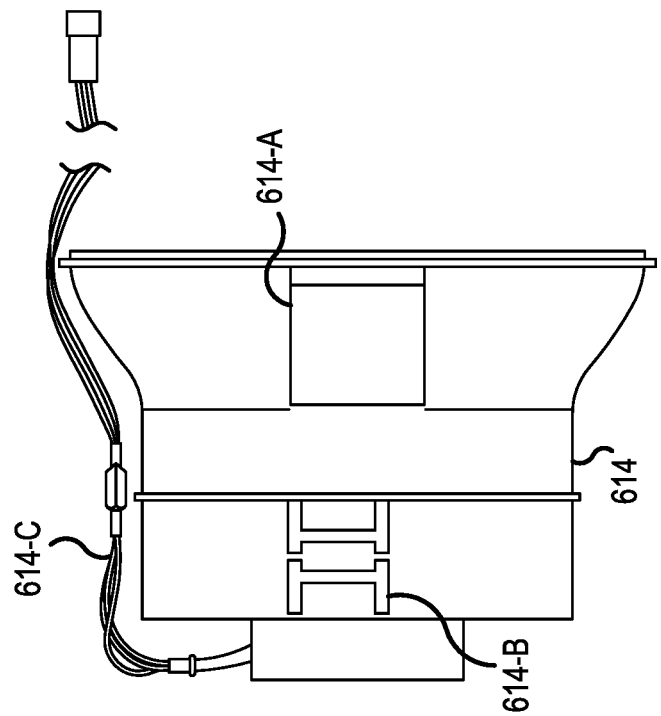
Figure 8B:
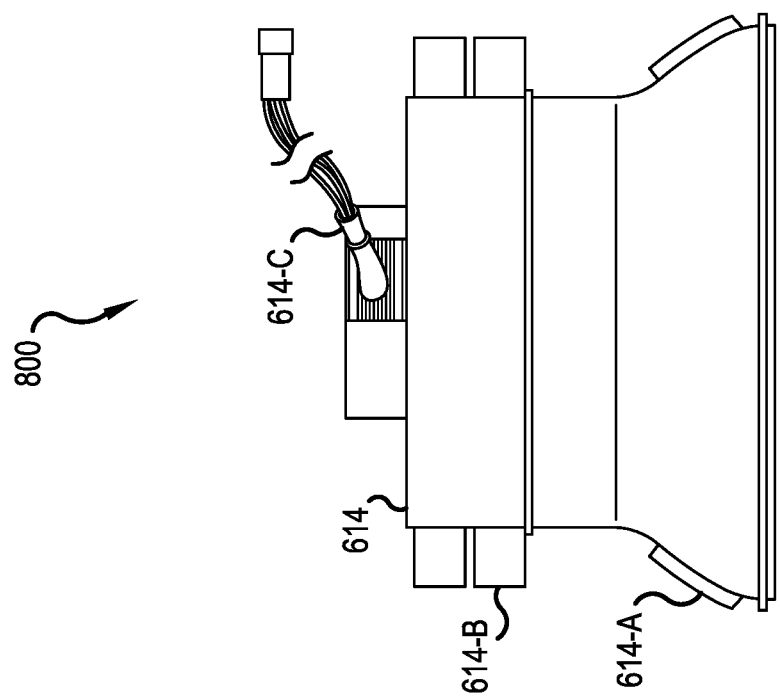

FIGS. 8A and 8B depict exemplary components of an exemplary handheld blower device having four spray nozzles relating to an electric turbine and its components.

Figure 9A:
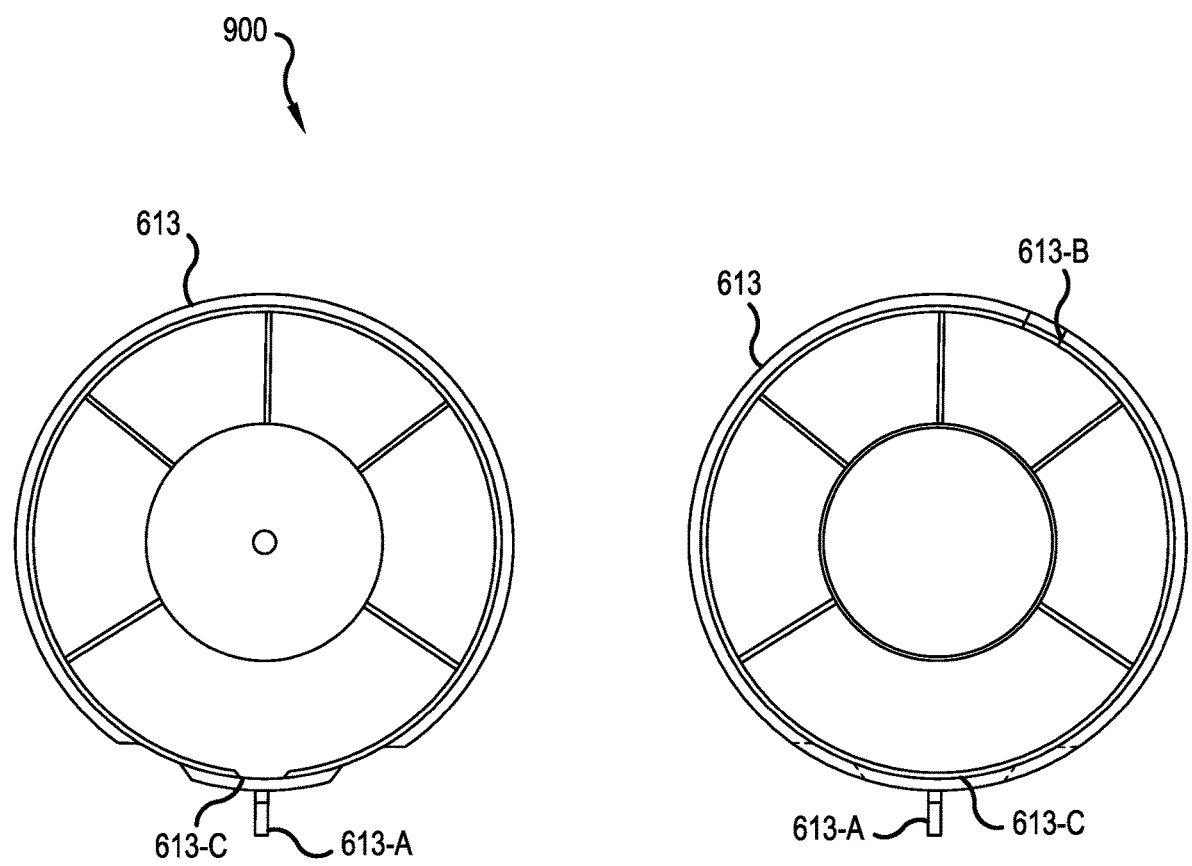
Figure 9B:
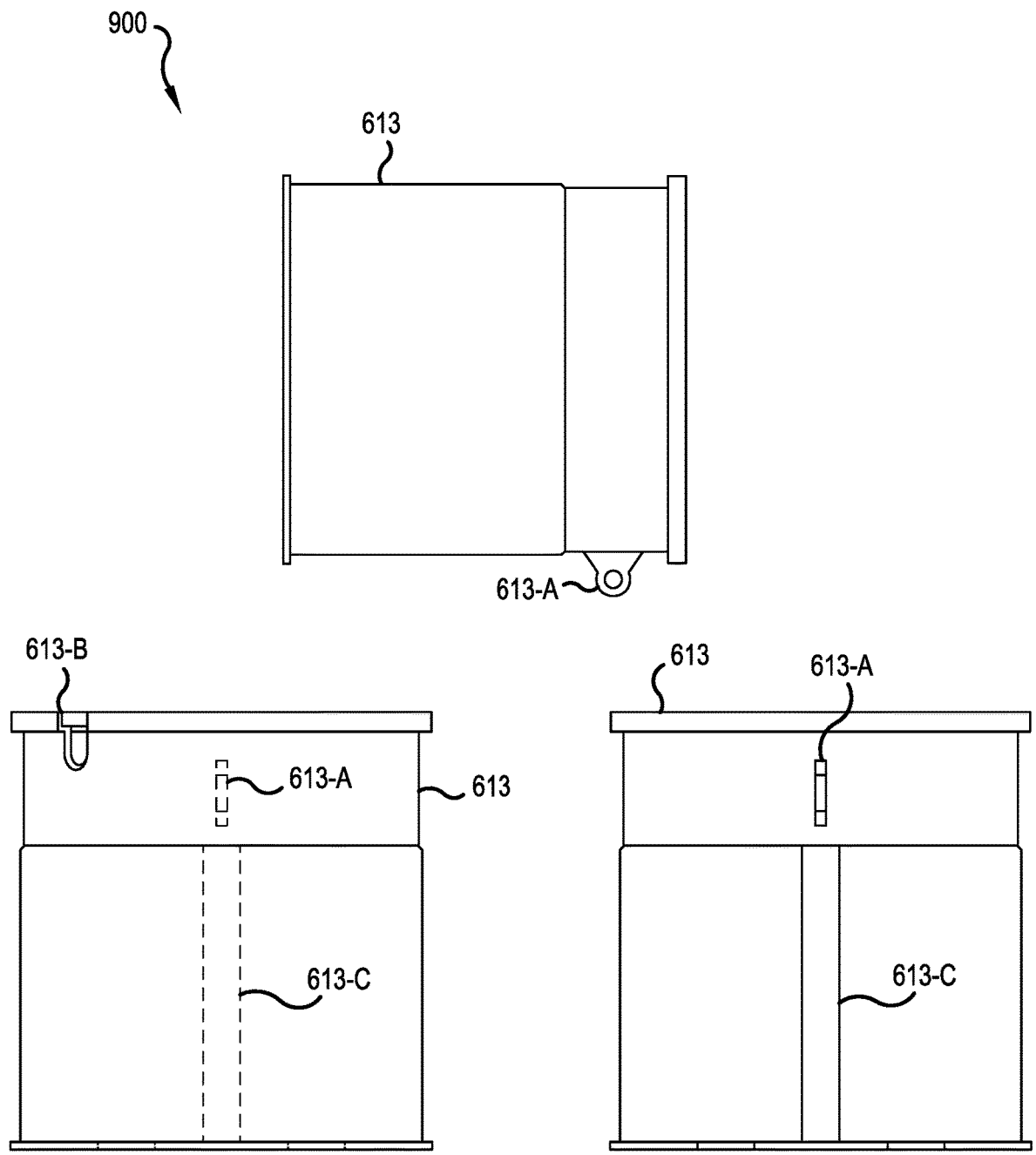

FIGS. 9A and 9B depict exemplary components of an exemplary handheld blower device having four spray nozzles relating to an air stream cone and its components.

Figure 10A:
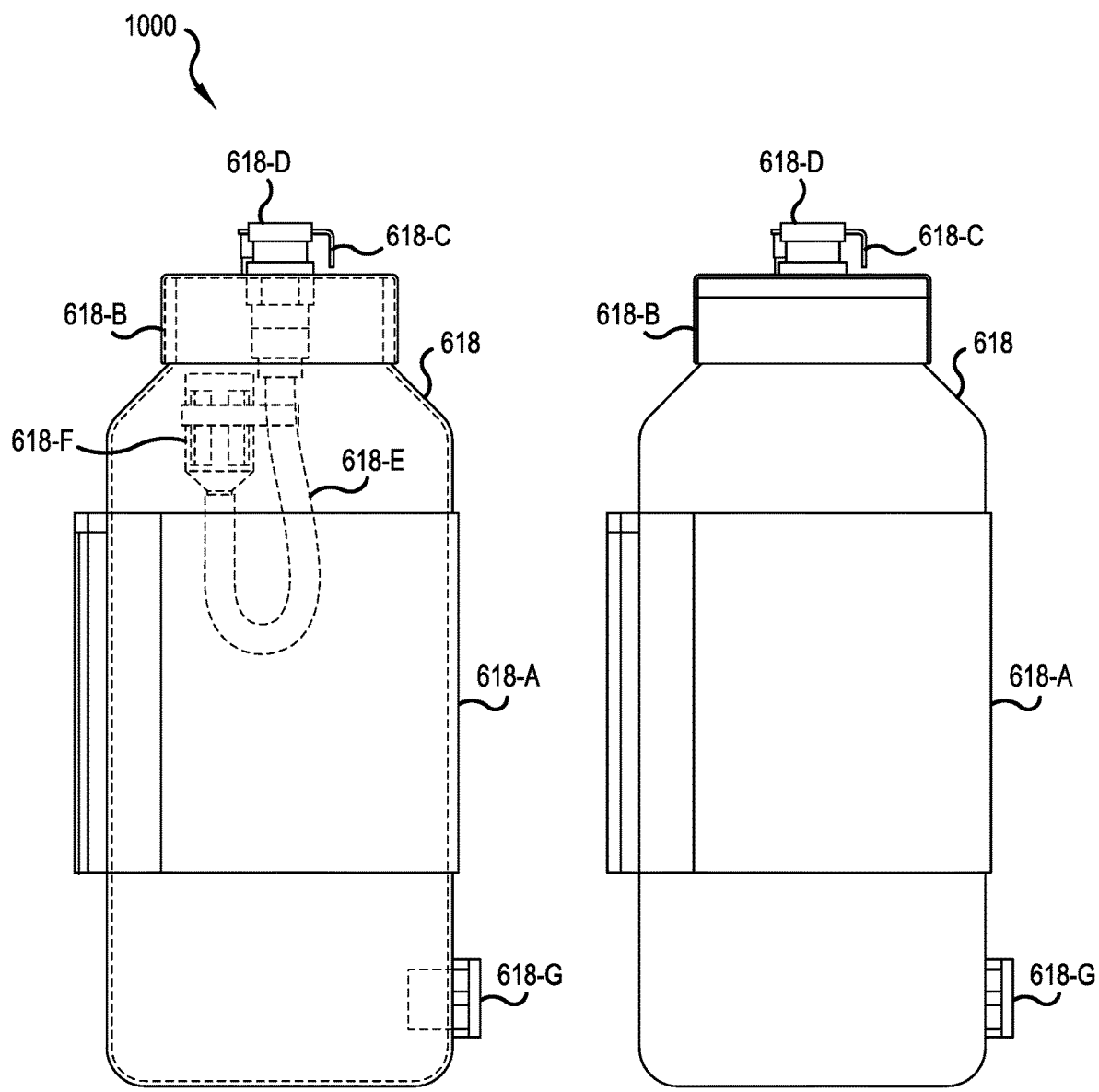
Figure 10B:
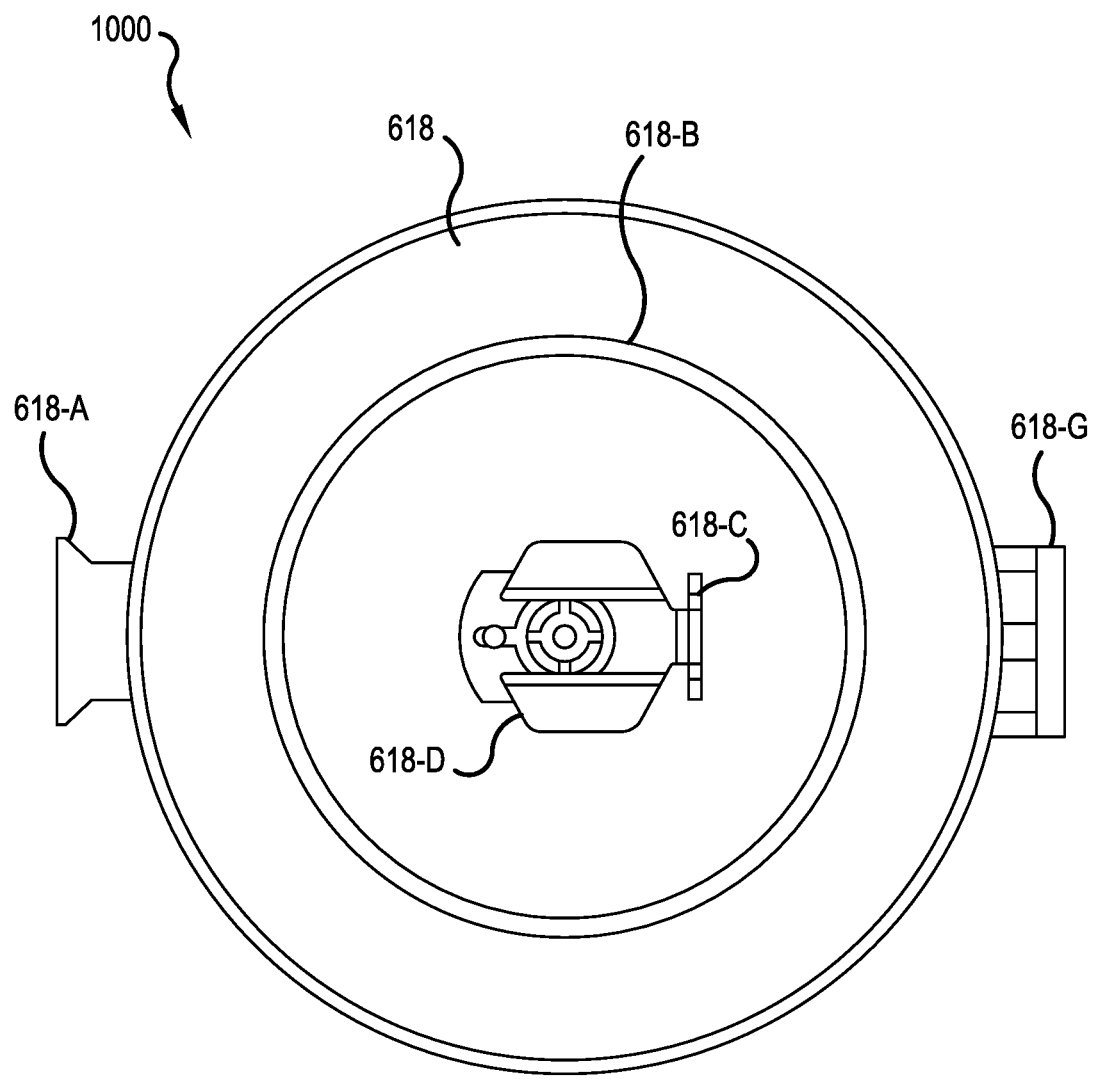

FIGS. 10A and 10B depict exemplary components of an exemplary handheld blower device having four spray nozzles relating to a solution bottle and its components.

FIG. 11A, 11B, 11C, 11D, 11E depicts a views of an exemplary handheld blower device having two spray nozzles and its components.

DETAILED DESCRIPTION OF THE INVENTION

Reference is made herein to the attached drawings. Like reference numerals may be used in the drawings to indicate like or similar elements of the description. The figures are intended for representative purposes and should not be considered limiting.

The present disclosure can be understood more readily by reference to the following detailed description of the present disclosure and the examples included therein.

Before the present articles, systems, devices, and/or methods are disclosed and described, it is to be understood that they are not limited to specific implementations unless otherwise specified, or to particular approaches unless otherwise specified, as such can, of course, vary. It is also to be understood that the terminology used herein is for the purpose of describing aspects only and is not intended to be limiting. Although any methods and materials similar or equivalent to those described herein can be used in the practice or testing of the present disclosure, example methods and materials are now described.

All publications mentioned herein are incorporated herein by reference to disclose and describe the methods and/or materials in connection with which the publications are cited.

Definitions

It is to be understood that the terminology used herein is for the purpose of describing particular aspects only and is not intended to be limiting. As used in the specification and in the claims, the term "comprising" can include the aspects "consisting of" and "consisting essentially of." Unless defined otherwise, all technical and scientific terms used herein have the same meaning as commonly understood by one of ordinary skill in the art to which this present disclosure belongs. In this specification and in the claims which follow, reference will be made to a number of terms which shall be defined herein.

As used in the specification and the appended claims, the singular forms "a," "an," and "the" include plural referents unless the context clearly dictates otherwise. Thus, for example, reference to "an opening" can include two or more openings.

Ranges can be expressed herein as from one particular value, and/or to another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

The terms "first," "second," "first part," "second part," and the like, where used herein, do not denote any order, quantity, or importance, and are used to distinguish one element from another, unless specifically stated otherwise.

As used herein, the terms "optional" or "optionally" means that the subsequently described event or circumstance can or cannot occur, and that the description includes instances where said event or circumstance occurs and instances where it does not. For example, the phrase "optionally affixed to the surface" means that it can or cannot be fixed to a surface.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including matters of logic with respect to arrangement of steps or operational flow; plain meaning derived from grammatical organization or punctuation; and the number or type of aspects described in the specification.

Disclosed are the components to be used to manufacture the disclosed devices, systems, and articles of the present disclosure as well as the devices themselves to be used within the methods disclosed herein. These and other materials are disclosed herein, and it is understood that when combinations, subsets, interactions, groups, etc. of these materials are disclosed that while specific reference of each various individual and collective combinations and permutation of these materials cannot be explicitly disclosed, each is specifically contemplated and described herein. For example, if a particular material is disclosed and discussed and a number of modifications that can be made to the materials are discussed, specifically contemplated is each and every combination and permutation of the material and the modifications that are possible unless specifically indicated to the contrary. Thus, if a class of materials A, B, and C are disclosed as well as a class of materials D, E, and F and an example of a combination material, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the articles and devices of the present disclosure. Thus, if there are a variety of additional steps that can be performed it is understood that each of these additional steps can be performed with any specific aspect or combination of aspects of the methods of the present disclosure.

It is understood that the devices and systems disclosed herein have certain functions. Disclosed herein are certain structural requirements for performing the disclosed functions, and it is understood that there are a variety of structures that can perform the same function that are related to the disclosed structures, and that these structures will typically achieve the same result.

Handheld Blower Devices, Systems, and Components

A function of any blower is creating and maintaining a stable thrust vector of the air-flow direction, velocity, and range. For this function in tandem with a variable speed controller creates an advantage giving the user variable coating control of the chosen coating location(s).

Heating elements operate through inducing electrical charge/electrons directly into a resistor structure, of which are mainly comprised of a metal or a metal alloy. As the electrons flow or propagate through the resistor's dense atomic structure, this in turn slows the electrical flow, constituting in a buildup of heat. In turn, an increase of this electrical-flow/input of the electrons constitutes a greater convection of the heat/heat-index. Certain appliances which comprise of an air conditioning system include hair dryers and countertop cooking appliances, and air fryers. These and similar devices communicate air that passes over a surface of a heating element and thereby heat and/or condition the local air column. Other examples include a hot plate used in cooking and a coffee brewer which includes a single snaked or wound resistor. In implementations of the present disclosure, a brushless DC (BLDC) motor may be used to heat a modular fan blade system through magnetic induction.

Mini-E: Superior Handheld Blowing

The axial blower fan creates a thrust vector, substantiating air direction and velocity. This function creates an advantage as it gives the operator control over direction and velocity, equaling greater coating control of the location(s). The axial blower includes an electronic variable speed control, such that a variable modulation of the blower speed may be achieved through use of a trigger, which allows for a user to adjust speed on the fly. A particular feature is a selector dial for selection of a desired speed. Axial is with the reference to the direction, same as a vector potential, the speed and direction of the flow. In essence, variable speed control is managed by an E.S.C/electronic speed controller which in turn manages the flow of electrons in a circuit. Pressure travel, whereby travel is the movement of the trigger by the finger force of the user which equals air speed, such that light pressure=slower flow of the electrons, and heavy pressure=faster flow of the electrons.

The diffuser or air flow stabilizer helps maintain a laminar flow from the axial blower fan. Laminar refers to a coherent flow of the air through a venturi or tapered constriction. The body of the Mini-E™ functions as the main venturi, while the diffuser maintains a coherent air flow. Blower fans chop the air, creating buffer zones or gaps in the airflow. In a sense the diffuser works as a set of mini wings making the airflow smoother.

The thrust vectoring diffuser contributes to the velocity and air speed with the specifications by the magnitude and direction of the flow. Vectoring involves the pivoting or motion with the physical diffuser, which equals control direction with the airflow. This grants the user an advantage, because the diffuser can be positioned to concentrate airflow in a desired direction, voiding of any need to tilt, turn, or adjust the unit. This function can be controlled through analog or digital actuation. In a general sense, vectoring controls the angle of which the air is flowing from the main-stator or axial blower fan through the venturi/shell of the Mini-E, which then contacts the surface wings/slats of the diffuser which diverts the air in the desired direction, either up or down.

The trigger assembly includes a trigger which controls the variable speed of the axial blower fan. The chargeable battery pack permits power flow to the components of the system. The boost button boosts velocity of the motor with the axial blower fan creating more air force for the coating range.

Picatinny rails may be included which provide a mounting platform for the various features, such as the lights, meters, and readouts, and the unit can be mounted with the mobile platforms such as with a truck or a robot, which may be a requirement for operation in certain hazardous locations.

UV light may be included which is harmful to bacteria and viruses. UV light may function as a sentry for the pre-treatment of incoming air.

Spray nozzles may be included which function in the atomization of the liquids and solutions into fine mist. The user can control the liquid flow through the flow valves with these positions on the top and bottom of the unit, respective to that nozzle. Users can control which nozzle set to use through these flow valves, giving greater control over the coating location and control of the solution particulate size, surfaces varies, and the capability to control particulate size is an advantage, whereby coatings being used will conform with the layout, albeit cracks, holes, fractures rough and/or smooth surfaces, for a superior coating coverage. In the listing below is the various nozzle function of each embodiment:

Mini-E, QUAD: four micro-spray nozzles atomize liquids into fine-mist. Users can control these through the flow valves with these positions on the top and bottom of the unit, respective to that nozzle. Top and bottom nozzles can be outfitted for a desired particle size, based on the user's preference and/or job application.

Mini-E, DUAL: two spray nozzles atomize liquids into fine mist. Top nozzle creates a heavier flow with the aerosol while the bottom generates lighter flow. Users can control these through the flow valves with these positions on the top and bottom of the unit, respective to that nozzle. Graphics pads may be positioned on the left side of this embodiment and illustrate the flow pattern of each nozzle. Top pad shows light spray and bottom pad shows heavy spray. Users can control which nozzle set to use through these flow valves, giving greater control over the coating location. Top and bottom nozzles can be outfitted for desired particle sizes, based on the user's preference and/or job-application.

Mini-E, DUAL: Peristaltic/Meter-Mixing-System/On-Demand-Mixing-System includes two spray nozzles which atomize liquids into fine mist. Top nozzle creates a heavier flow with the aerosol while the bottom generates lighter flow. Users can control these through the flow valves with these positions on the top and bottom of the unit, respective to that nozzle. Graphics pads may be positioned on the left side of this embodiment and illustrate the flow pattern of each nozzle. Top pad shows light spray and bottom pad shows heavy spray. Users can control which nozzle set to use through these flow valves, giving greater control over the coating location. Top and bottom nozzles can be outfitted for desired particle-sizes, based on the user's preference and/or job application.

A peristaltic pump creates positive placement or time release of the concentrate through a rotary motion/analog or by a digital signaling of a roller with which contacts with a flexible-tube, pinching said tube, creating a meter-flow of the concentrate. Peristaltic-mechanics can be fine-tuned to mix high-concentrate-disinfectant-compositions without the need to pre-mix. In addition, a mixing chamber may be positioned at a central location where the water and concentrate mix.

Referring now to FIG. 1A, there is depicted a front cross-sectional view of an exemplary heatable fan blade component in the form of a four-pole modular rotor (1400A). With reference to air-conditioning/heating mechanics of the device, for the heating of a local air column within the device, an induction interaction is generated between an alternating magnetic field generated by the stator (14-E of FIG. 1B) coil configuration (which acts as a transmission coil) and the receiver coil (14-D2). During this process, the alternating magnetic field of the stator transfers electrical current within the receiver coil (14-D2), which powers the oscillator circuit (14-D4) which regulates the electrical current through the receiver coil (14-D2). The electrical current passes through the receiver lead lines (14-D3) wound with the stator supports (14-D5) and resistor puck mounting braces (14-D6) connecting to the resistor pucks (14-D7). As current passes through the resistor pucks (14-D7) this in turn increases the heat index within the cavity of the fan blades (14-D), whereby the rotation of the rotor (14-D10) and fan blades (14-D) heats the local air column and in turn the rotation acts as a heat sink for the fan blades (14-D).

Referring now to FIG. 1B, 1400B there is depicted a front cross-sectional view of the four-pole modular rotor which includes a non-conductive material with seven symmetrically spaced fan blades. Mounted within the rotor are four permanent magnets that are symmetrically spaced and of different dipolar-configurations (Permanent-Magnet-A=North, Permanent-Magnet-B=South, Permanent-Magnet-A=North, Permanent-Magnet-B=South), which interact with the stator to create rotation. In various implementations, a BLDC motor is used in devices and systems of the present disclosure. A six-pole stator (14-E) is shown which includes a circular disk constructed of a non-conductive material with six symmetrically-spaced stator support columns (14-E1) extruded along the edge of the disk, in which filaments (14-E2) are wound with the stator support columns (14-E1) in a specific direction, creating a magnetic north pole/START-1 and connecting by a lead-filament (14-E3) wound in the opposite direction to an adjacent stator support column (14-E1) to create a magnetic south pole/END-1 of which equates to a coil or COIL-1. This winding process is repeated with each stator support column (14-E1) of which START-2/NORTH to END-2/SOUTH=COIL-2, START-3/NORTH to END-3/SOUTH=COIL-3 to create a three-phase motor configuration. The totality of these windings creates a coil configuration. For the streaming of the direct current through a coil, which energizes that coil and creates an electromagnet/magnetic field. Through the alternation of these magnetic states in each coil by a Hall sensor (14-E4) on a bread board (14-E5) this creates a simple force mechanic of the potentials between the permanent magnets (14-D8) of the rotor (14-D10) and with the stator (14-E) this creates rotation of the rotor (14-D10). Revolutions of the rotor (14-D10) at slower speeds are tracked with better efficiency by the speed sensor strip (14-D6) through the magnetic field from Is the permanent magnets (14-D8).

Referring now to FIG. 2, there is depicted a side view of an exemplary modular heatable blade coupled with a rotor. With reference to the coupling functions of the modular heatable fan blade (e.g., that includes an additional embodiment of the integrated heated fan blade embodiment within the device). A modular heatable fan blade (100) is coupled with a fan rotor (5). The modular heatable fan blade (100) external features include a light-emitting diode (LED) sheath (1) and quick-connect coupling (2). The modular heatable fan blade (100) has dual purposes and acts in tandem with the resistor puck (1C of FIG. 5) as a transfer element of the heat and structural support with the outer and internal electronic components of the modular heatable fan blade (100). For this conceptualization of the fan rotor (5), external features include the LED sheath (6) and integrated low-profile coupling hub (3).

Referring now to FIG. 3, there is depicted a side view of a swapping of the modular heatable fan blade (100) with a finger-gripping of a quick-connect coupling and performing an upward motion with the quick-connect coupling, which actuates tension spring(s) and frees the heatable fan blade from a low-profile coupling hub. The swapping of the modular heatable fan blade (100) may be performed with a finger gripping of the quick-connect coupling (2) and performing an upward-motion with the quick-connect coupling (2) which actuates the tension springs (2A of FIG. 5) and in the tandem recesses the detent balls (2B of FIG. 5), thereby freeing the modular heatable fan blade from the low-profile coupling hub (3). For this implementation of the rotor (5) there is shown external features which include an LED sheath (6) and integrated low profile coupling hub (3). For this implementation, these closures is with a single coupling method, but in alternate implementations, may use a twist-lock/coupling, a pin-lock/coupling, a magnetic coupling, a threaded fastening, a form-fit, and/or a snap-fit.

Figure 3:
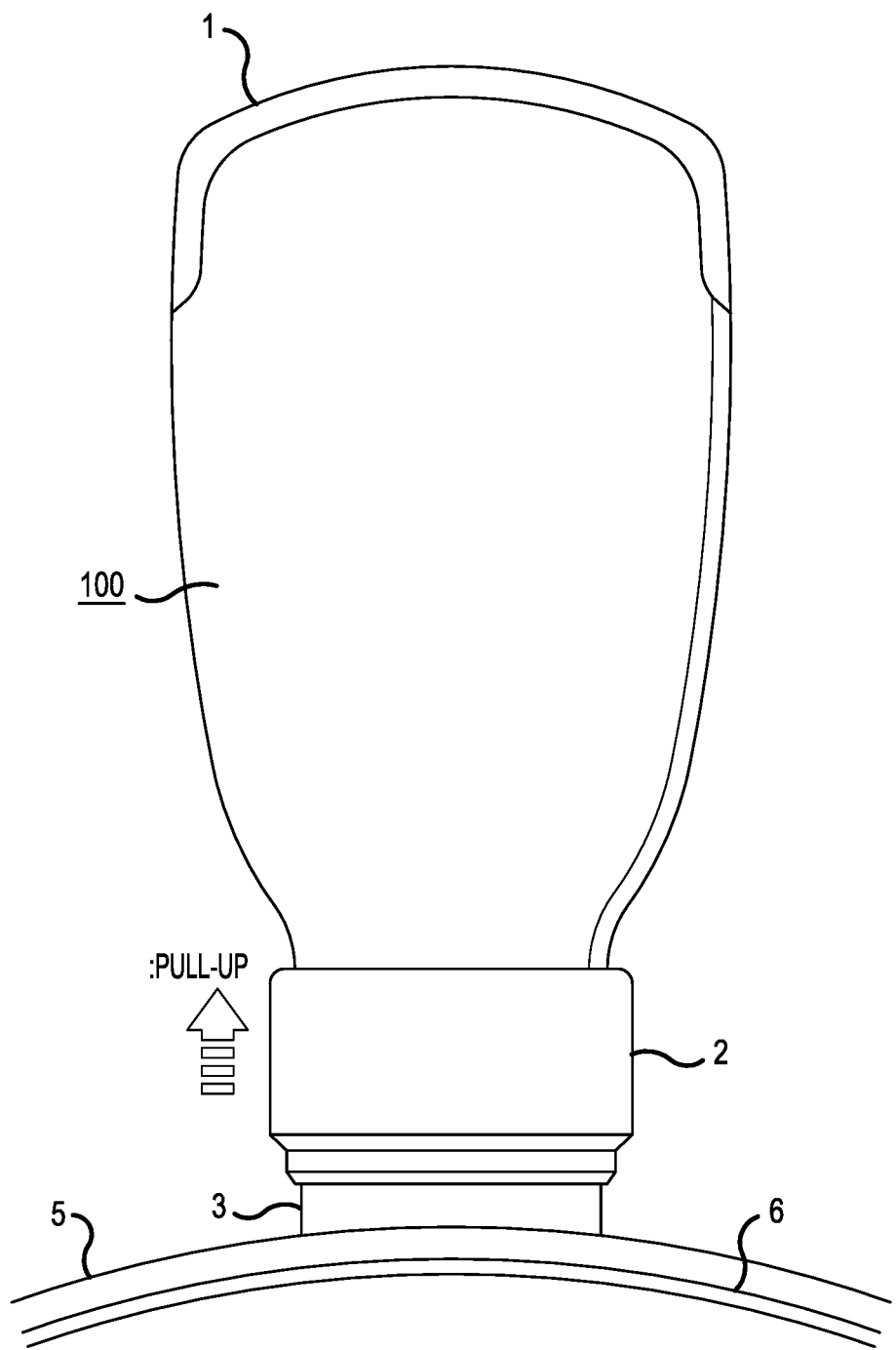
FIG. 3 depicts a side view of a swapping of the modular heatable fan blade with a finger-gripping of a quick-connect coupling and performing an upward motion with the quick-connect coupling, which actuates tension spring(s) and frees the heatable fan blade from a low-profile coupling hub.
Figure 3A:
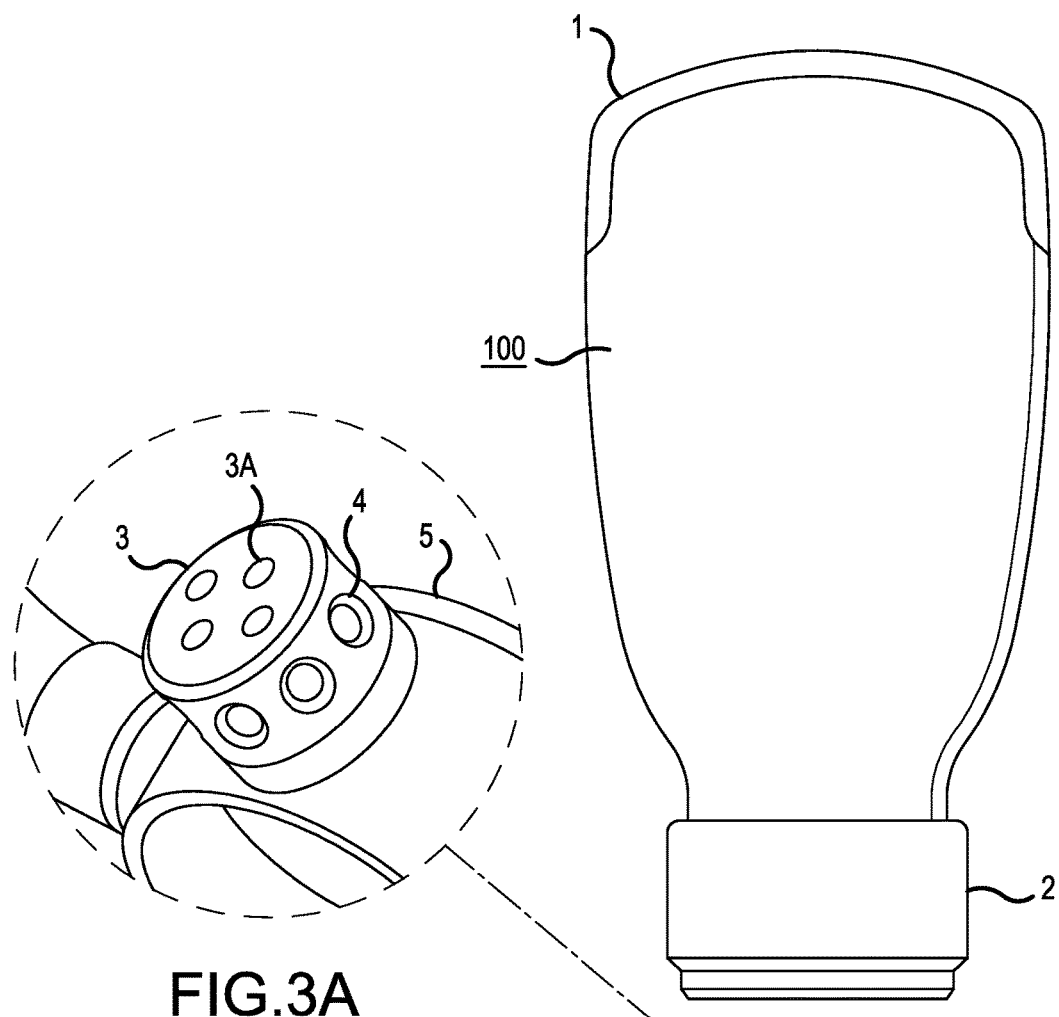
FIG. 3A is a close-up perspective view the low-profile coupling hub.
Figure 4:
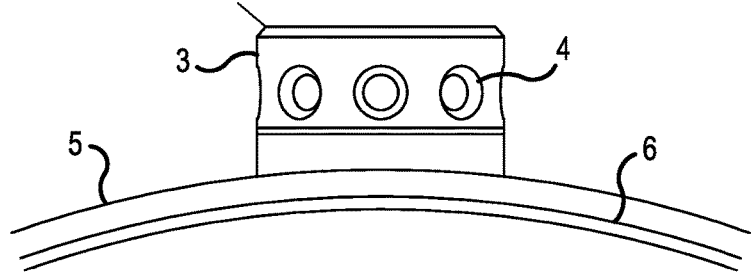
FIG. 4 depicts a side view and a close-up perspective view of a separation of the modular heatable fan blade from the rotor to reveal the low-profile coupling hub and external features of a female power transfer communication plate and a detent notch.

Referring now to FIG. 3A and FIG. 4, there is depicted a side view and a close-up perspective view of a separation of the modular heatable fan blade (100) from the rotor to reveal the low-profile coupling hub and external features of a female power transfer communication plate and a detent notch. The modular heatable fan blade (100) may be separated from the fan rotor (5) to uncover the low-profile coupling hub (3). The low-profile coupling hub (3) external features includes a female power transfer communication plate (3A) and detent notch (4).

Figure 1A:
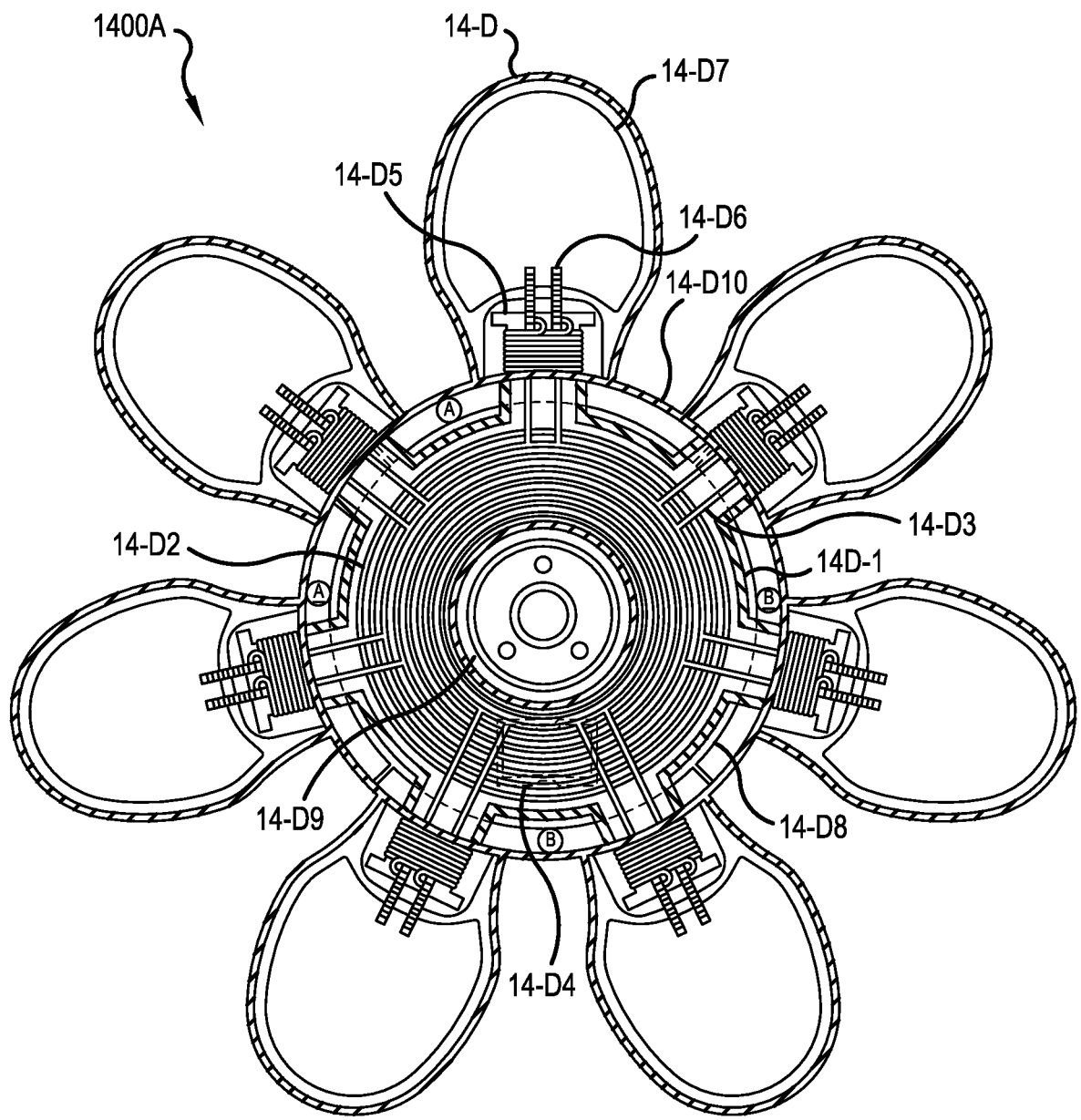
FIG. 1A depicts a front cross-sectional view of an exemplary heatable fan blade component in the form of a four-pole modular rotor.
Figure 1B:
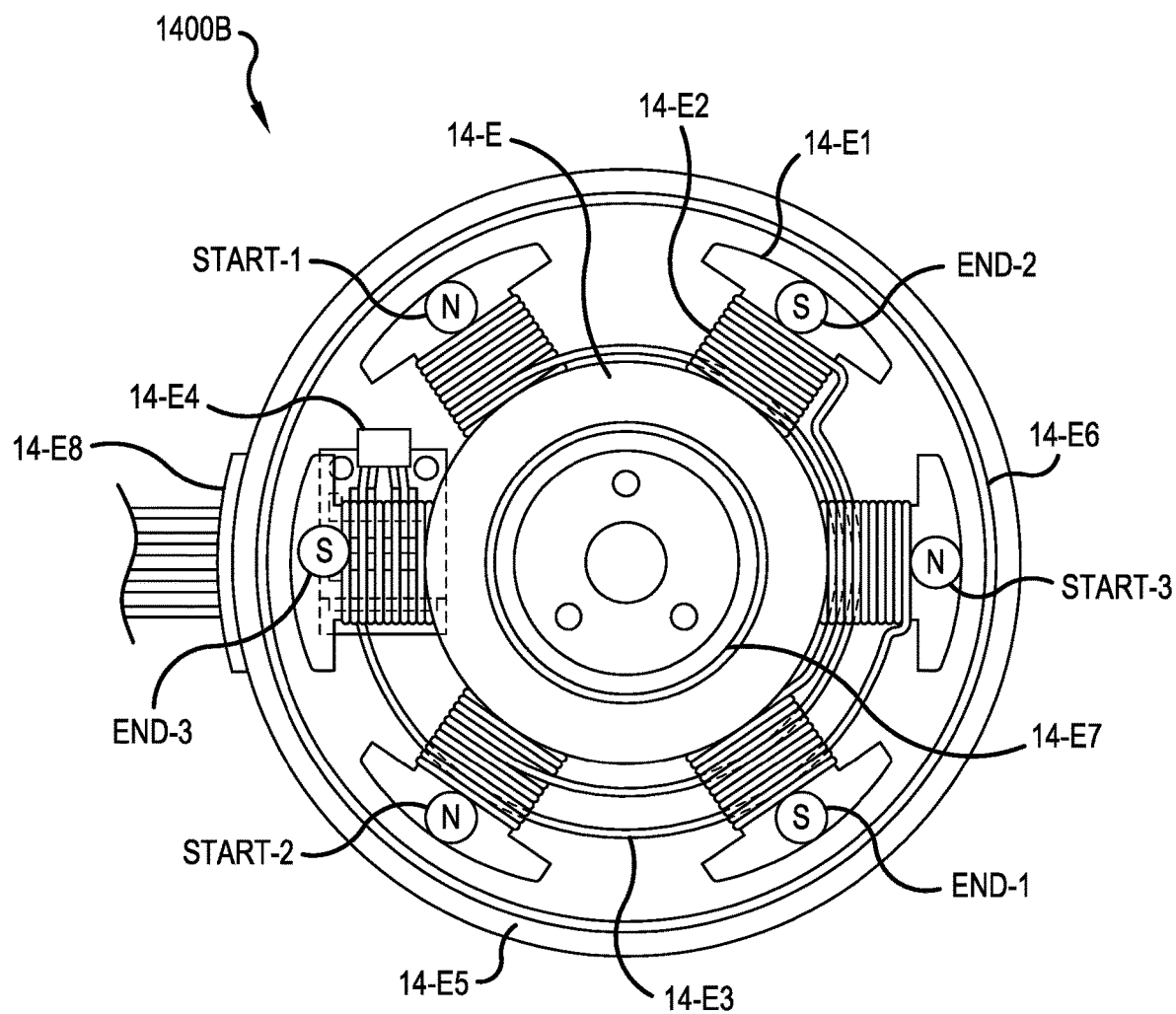
FIG. 1B depicts a front-view of the six-pole-stator of an exemplary handheld blower device.
Figure 2:
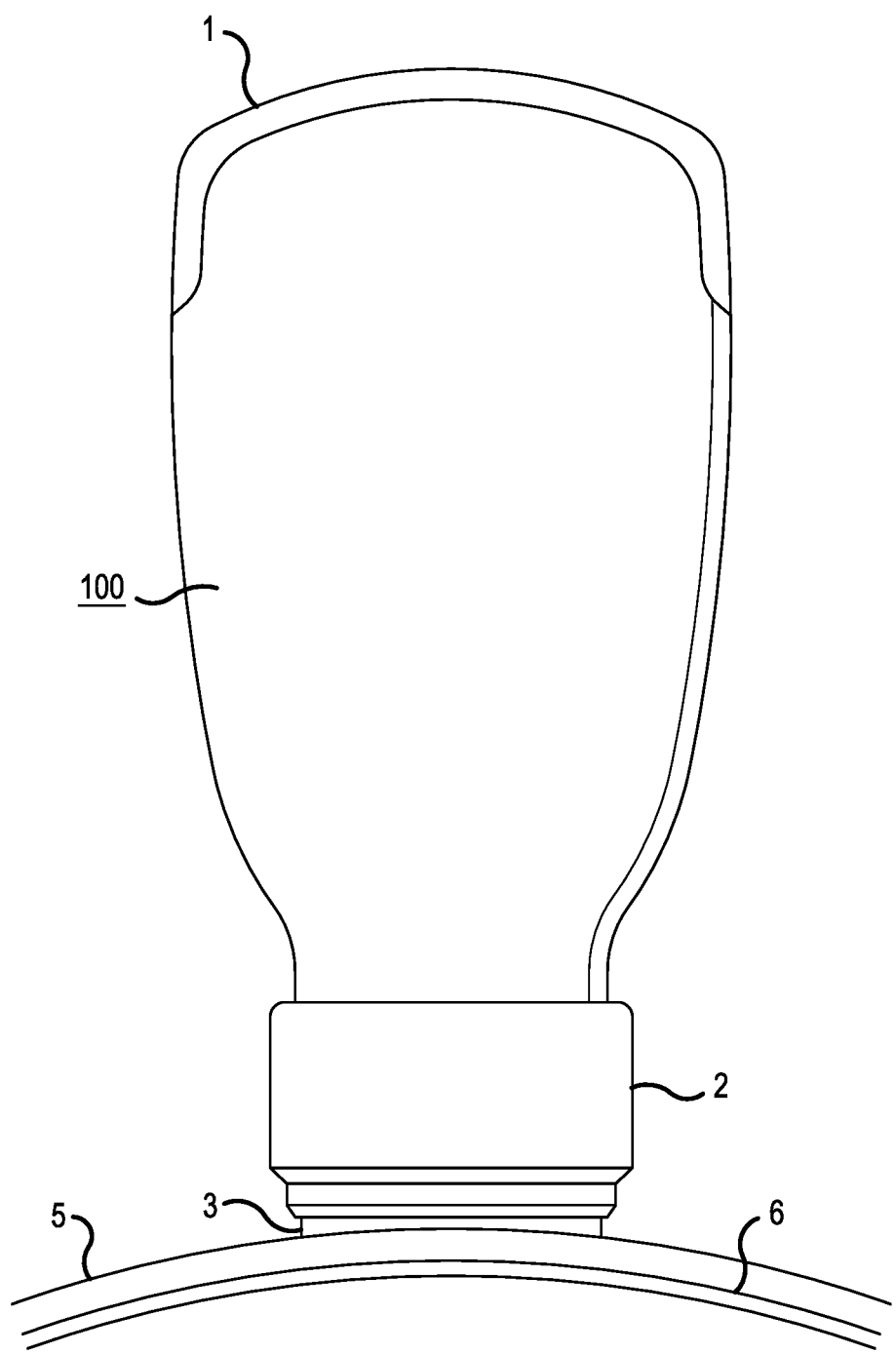
FIG. 2 depicts a side view of an exemplary modular heatable blade coupled with a rotor.

Referring now to FIG. 5, there is depicted a cross-section-view of the modular heatable fan blade (100) with closures of the internal structure and other components. The modular heatable fan blade is heated through an electrical resistive mechanic mechanism whereby electricity passes through a resistive material and the atomic structure of the material slows propagation of the electron flow, creating friction which results in heat. For the shown embodiment, the modular heatable fan blade is shown coupled with the low-profile coupling hub of the unit. In the shown embodiment, enclosures of the internal structure and components are shown. The modular heatable fan blades may be heated through an electrical resistive mechanic mechanism by which electricity passes through a resistive material and the atomic structure of the said material slows propagation with the electrons flow, creating friction which results in heat. For this embodiment, the modular heatable fan blade (100) is coupled with the low-profile coupling hub (3) of the unit. The modular heated fan blade (100) includes LED (1A), heat insulation (1B), resistor puck (1C), resistor mounting bracket (1D), LED power line (9), male power transfer communication plate (1E), quick connect coupling (2) tension springs (2A), and detent balls (2B). The low-profile coupling hub (3) includes detent notches (4), female power transfer communication plate (3A), and wire windings (7). The fan rotor (5) includes receiver coil (8), LED (6), and oscillator circuit (14-D4 of FIG. 1).

Figure 6A:
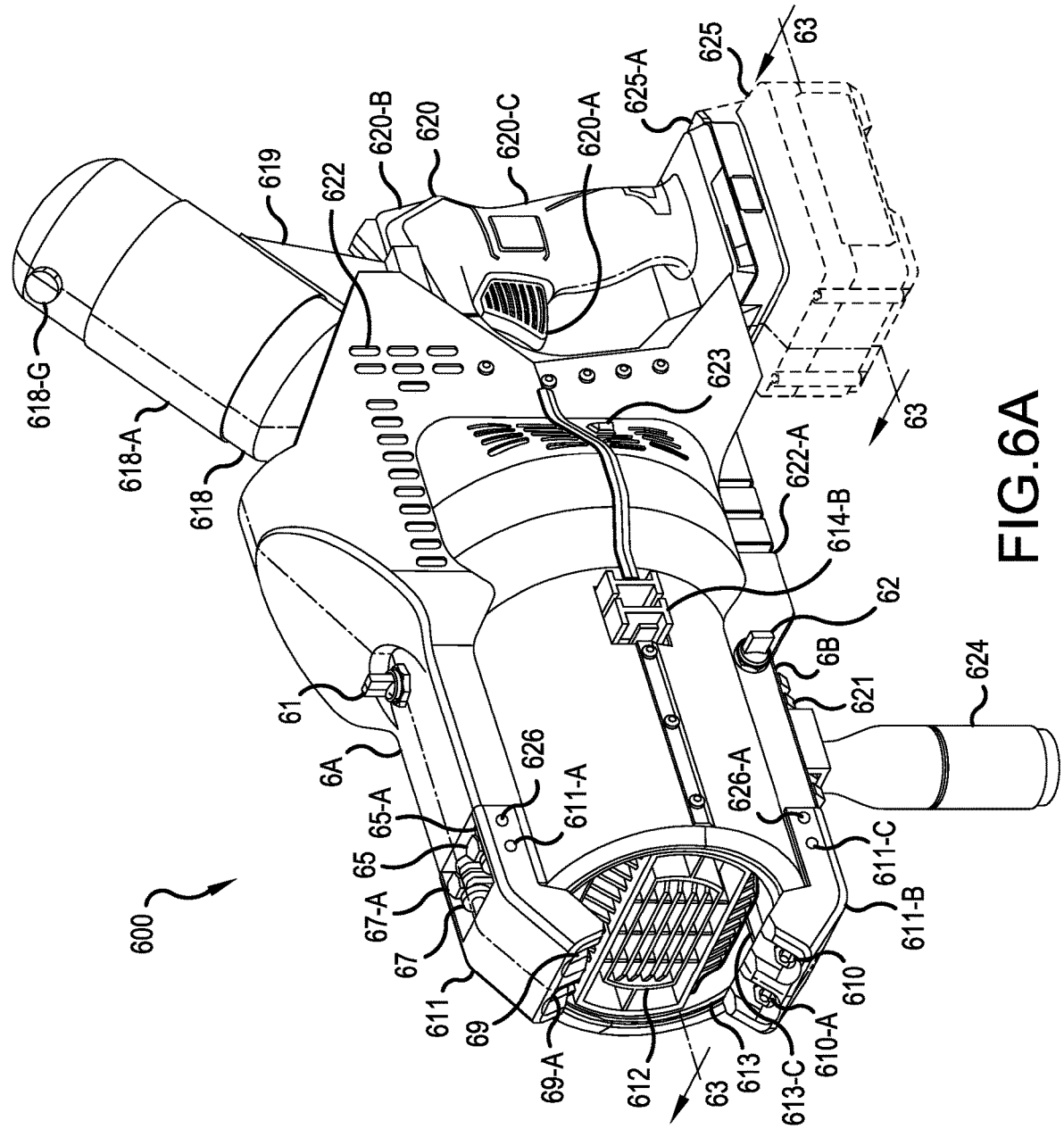

Referring now to FIG. 6A, there is depicted a perspective view of an exemplary handheld blower device having four spray nozzles, the Mini E Quad (600). The handheld blower device having four spray nozzle 600 comprises the following components:

6A: TOP-SOLUTION-LINE-CAVITY.
61: TOP-SHUT-OFF-VALVE.
61-A: TOP-SOLUTION-LINE.
61-B: RIGHT-SOLUTION-LINE.
61-C: LEFT-SOLUTION-LINE.
61-D: RIGHT-SOLUTION-LINE.

-continued

61-E: LEFT-SOLUTION-LINE.
6B: BOTTOM-SOLUTION-LINE-CAVITY.
62: BOTTOM-SHUT-OFF-VALVE.
62-A: BOTTOM-SOLUTION-LINE.
62-B: RIGHT-SOLUTION-LINE.
62-C: LEFT-SOLUTION-LINE.
62-D: RIGHT-SOLUTION-LINE.
62-E: LEFT-SOLUTION-LINE.
63: TOP-THREE-WAY-SPLITTER.
64: BOTTOM-THREE-WAY-SPLITTER.
65: LEFT-QUICK-CONNECT.
65-A: QUICK-RELEASE-BUTTON.
66: RIGHT-QUICK-CONNECT.
66-A: QUICK-RELEASE-BUTTON.
67: LEFT-QUICK-CONNECT.
67-A: QUICK-RELESE-BUTTON.
68: RIGHT-QUICK-CONNECT.
68-A: QUICK-RELEASE-BUTTON.
69: LEFT-SPRAY-NOZZLE.
69-A: RIGHT-SPRAY-NOZZLE.
610: LEFT-SPRAY-NOZZLE.
610-A: RIGHT-SPRAY-NOZZLE.
611: TOP-CAP.
611-A: SECURE-FIT-HOLES.
611-B: BOTTOM-CAP.
611-C: SECURE-FIT-HOLES.
612: FINGER-GUARD.
612-A: SPACE-INDENTION.
613: AIR-STREAM-CONE.
613-A: SCREW-MOUNT.
613-B: WIRE-PASS-THROUGH.
613-C: SPACER.
614: ELECTRIC-TURBINE.
614-A: SECURE-PADS.
614-B: SUPPORT-TRUSS.
614-C: TURBINE-WIRING.
614-D: TURBINE-FAN-BLADES.
614-E: TUBINE-AIR-FINS.
615: SOLUTION-PUMP.
615-A: MAIN-SOLUTION-LINE.
615-B FEED-LINE.
616: BRASS-THREE-WAY-SPLITTER.
617: CIRCUIT-BOARD/ CONTROLLER.
618: SOLUTION-BOTTLE.
618-A: MOUNT-GRIP.
618-B: BOTTLE-TOP.
618-C: QUICK-RELEASE-BUTTON.
618-D: QUICK-CONNECT.
618-E: SOLUTION-LINE.
618-F: FLUID-PICK-UP.
618-G: ONE-WAY-VALVE.
619: BOTTLE-BRACKET.
619-A: BOTTLE-CONNETION.
620: HANDLE-GRIP.
620-A: TRIGGER.
620-B: AIR-BOOST-BUTTON.
620-C: RUBBER-GRIP.
620-D: TRIGGER-ACTUATOR
620-E: CIRCUIT-BOARD.
620-F: BATTERY-TERMINAL-ARRAY.
621: PIKATINNY-RAIL.
622: SIDE-VENTS.
622-A: BOTTOM-VENTS.
623: POWER-SWITCH.
624: GRIP-HANDLE.
625: BATTERY.
625-A: QUICK-RELEASE.
626: ~TOP-CAP-MOUNT-TABS.
626-A: BOTTOM-CAP-MOUNT-TABS

Figure 6B:
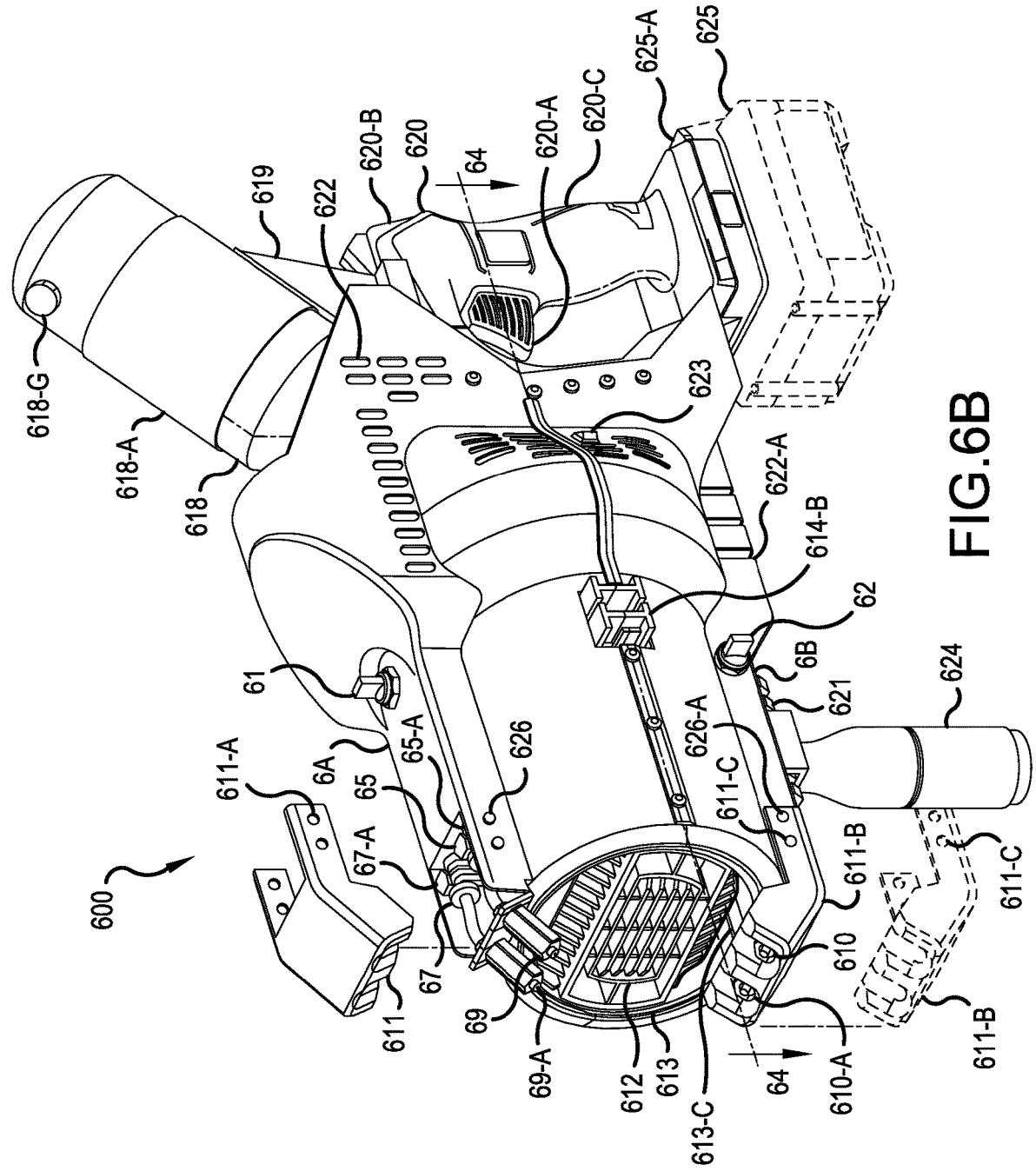
Figure 6C:
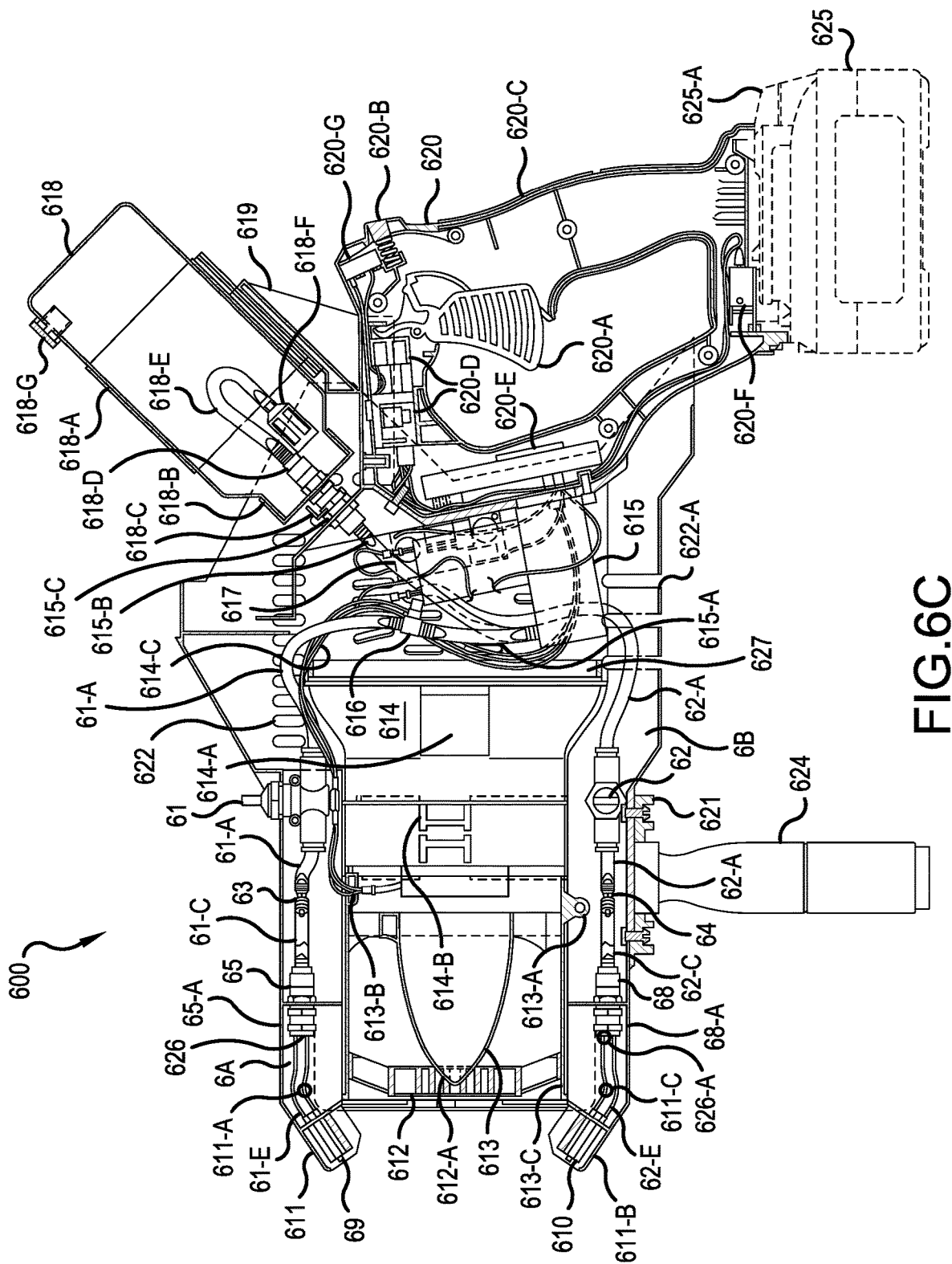
Figure 6D:
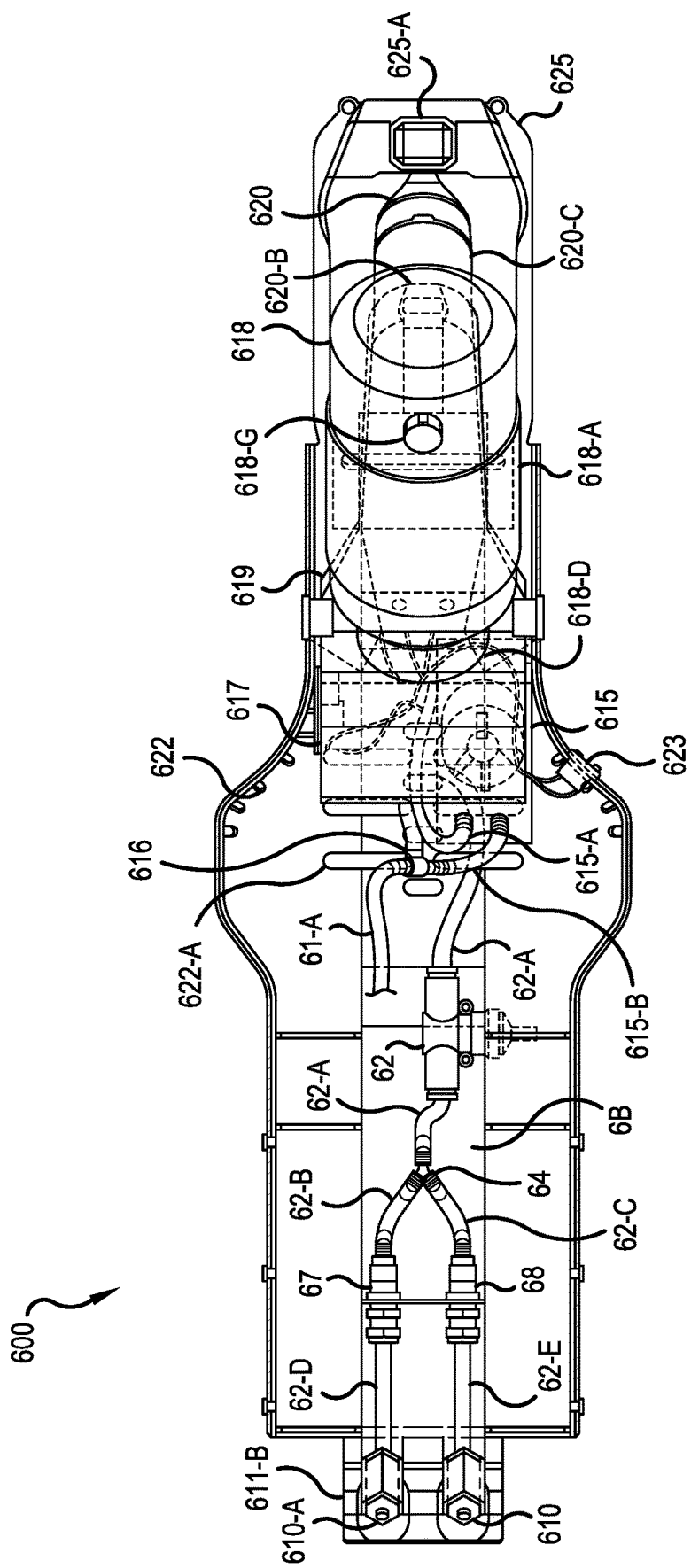
Figure 6E:
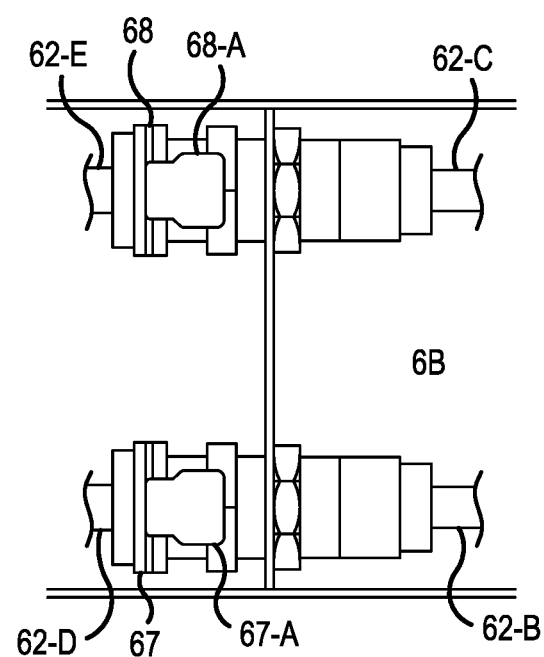
Figure 6F:
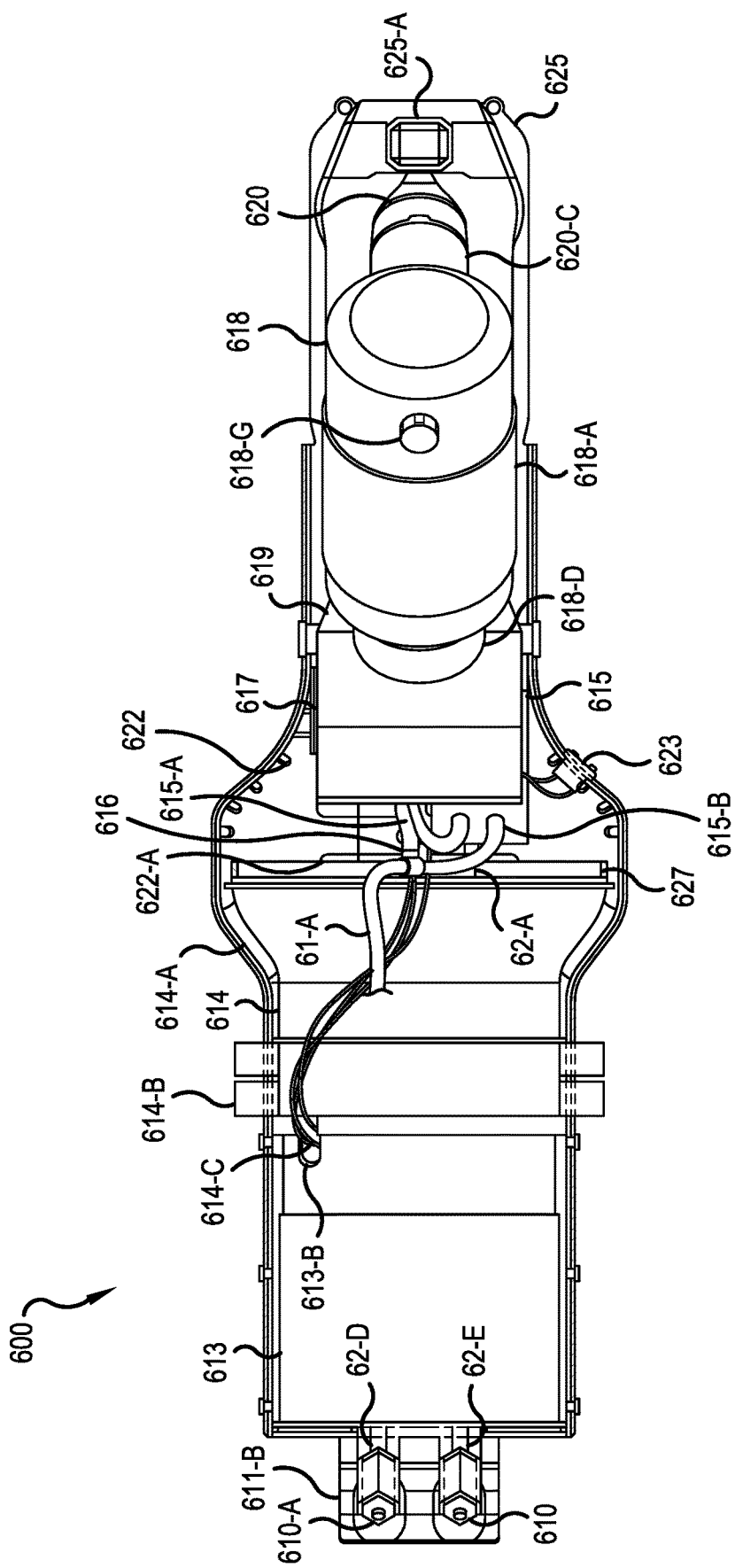
Figure 6G:
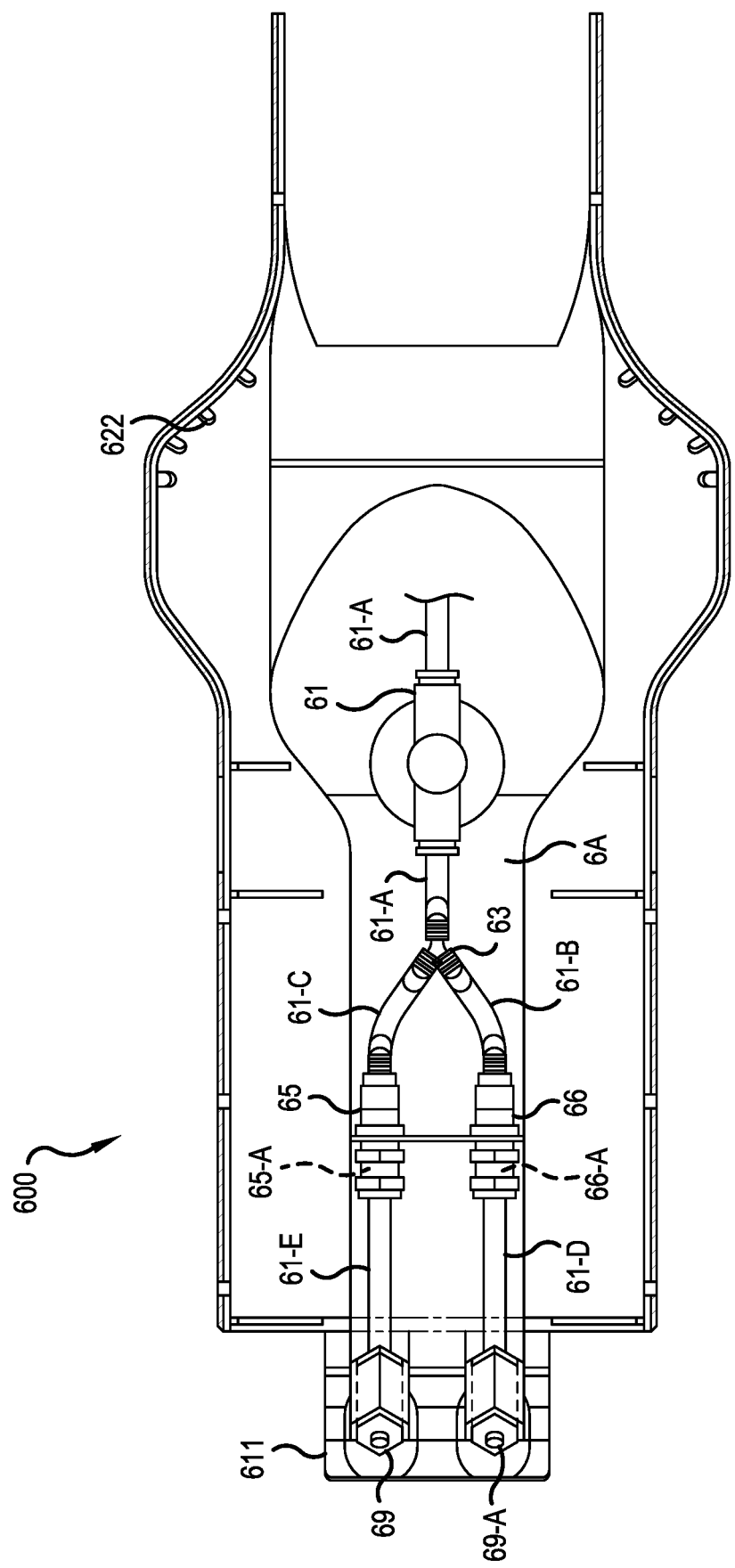
Figure 6H:
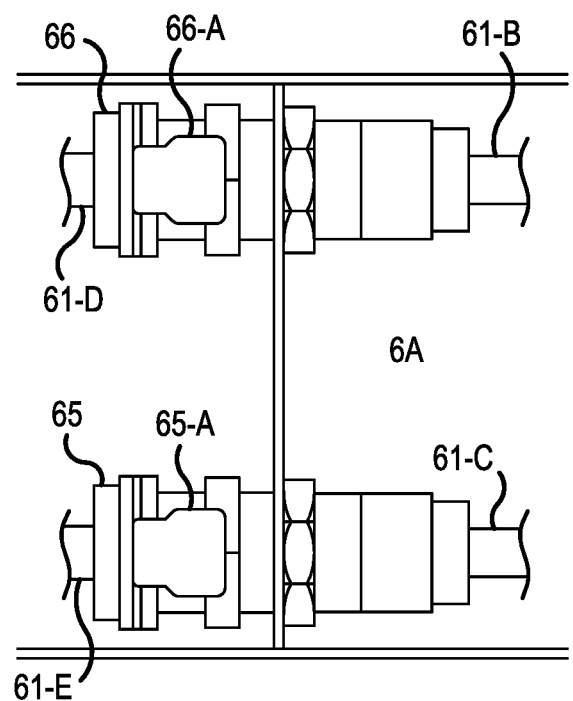

FIG. 6A depicts a perspective view of an exemplary handheld blower device having four spray nozzles 600, also known as the Mini-E Quad™. FIG. 6B depicts an exploded perspective view of an exemplary handheld blower device having four spray nozzles 600 showing the numbered components. FIG. 6C depicts a cross-sectional view of an exemplary handheld blower device having four spray nozzles 600 showing the numbered components. FIGS. 6D and 6E depicts a cross-sectional view bottom view of an exemplary handheld blower device having four spray nozzles 600 showing the numbered components. FIGS. 6F, 6G, and 6H depicts a cross-sectional view top view of an exemplary handheld blower device having four spray nozzles 600 showing the numbered components.

Referring now to FIG. 7, there is depicted an exemplary component of an exemplary handheld blower device 600 having four spray nozzles relating to a finger guard 612 and its components.

Referring now to FIGS. 8A and 8B there are depicted exemplary components of an exemplary handheld blower device 600 having four spray nozzles relating to an electric turbine 614 and its aforementioned components.

Referring now to FIGS. 9A and 9B there are depicted exemplary components of an exemplary handheld blower device 600 having four spray nozzles relating to an air stream cone 613 and its aforementioned components.

Referring now to FIGS. 10A and 10B there are depicted exemplary components of an exemplary handheld blower device 600 having four spray nozzles relating to a solution bottle 618 and its aforementioned components.

Figure 11A:
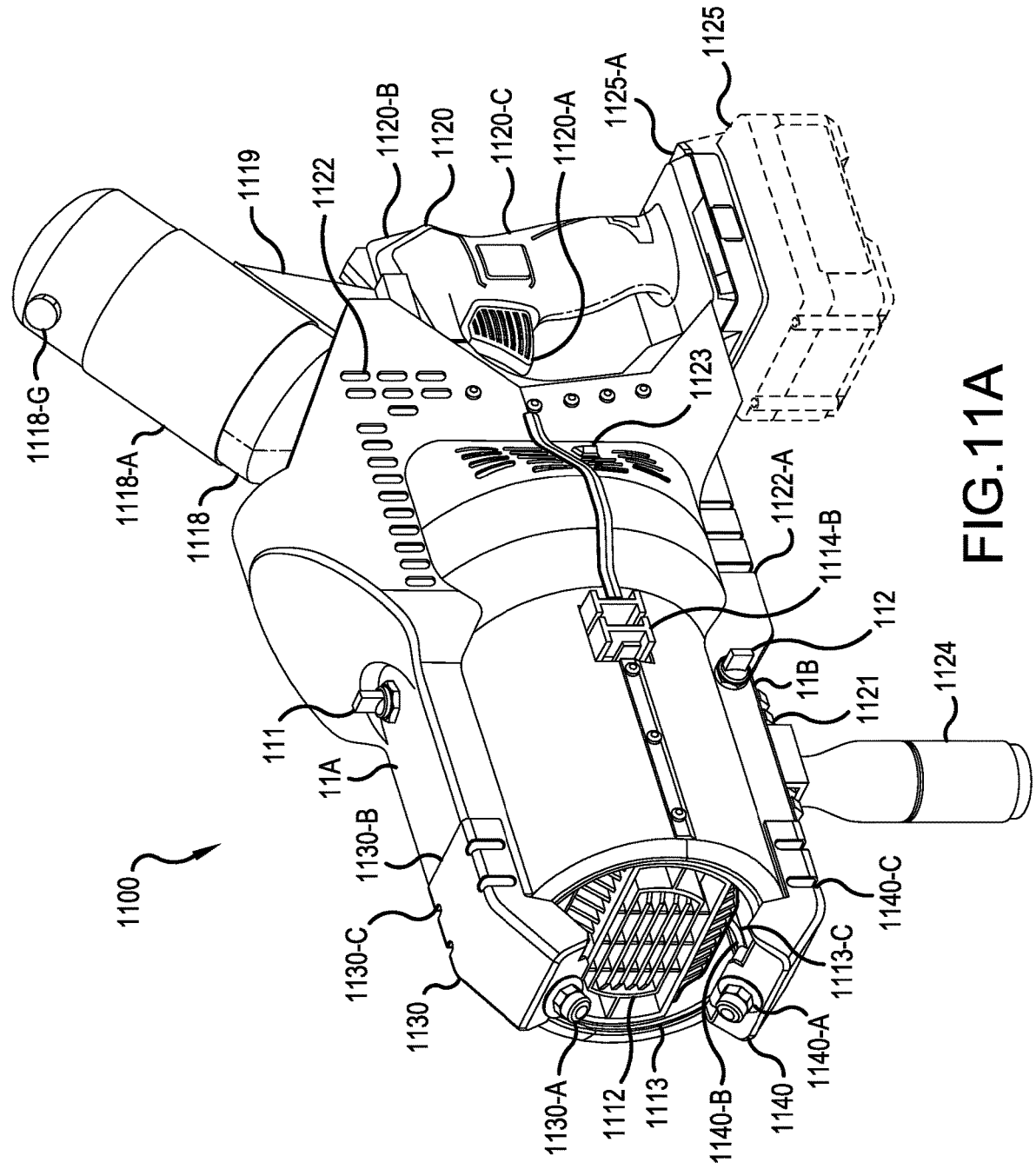

Referring now to FIG. 11A, 11B, 11C, 11D, 11E depicts views of an exemplary handheld blower device having two spray nozzles 1100 and its components. Referring now to FIG. 11A, there is depicted a perspective view of an exemplary handheld blower device having two spray nozzles 1100, also known as the Mini-E Dual. The handheld blower device having two spray nozzle 1100 comprises the following components:

11A: TOP-SOLUTION-LINE-CAVITY.
111: TOP-SHUT-OFF-VALVE.
11-A: TOP-SOLUTION-LINE.
111-B: RIGHT-SOLUTION-LINE.
111-C: LEFT-SOLUTION-LINE.
111-D: RIGHT-SOLUTION-LINE.
111-E: LEFT-SOLUTION-LINE.
11B: BOTTOM-SOLUTION-LINE-CAVITY.
112: BOTTOM-SHUT-OFF-VALVE.
112-A: BOTTOM-SOLUTION-LINE.
112-B: RIGHT-SOLUTION-LINE.
112-C: LEFT-SOLUTION-LINE.
112-D: RIGHT-SOLUTION-LINE.
112-E: LEFT-SOLUTION-LINE.
113: TOP-THREE-WAY-SPLITTER.
114: BOTTOM-THREE-WAY-SPLITTER.
115: LEFT-QUICK-CONNECT.
115-A: QUICK-RELEASE-BUTTON.
116: RIGHT-QUICK-CONNECT.
116-A: QUICK-RELEASE-BUTTON.
117: LEFT-QUICK-CONNECT.
117-A: QUICK-RELESE-BUTTON
118: RIGHT-QUICK-CONNECT.
118-A: QUICK-RELEASE-BUTTON.
119: LEFT-SPRAY-NOZZLE.
119-A: RIGHT-SPRAY-NOZZLE.
1110: LEFT-SPRAY-NOZZLE.
1110-A: RIGHT-SPRAY-NOZZLE.
1111: TOP-CAP.
1111-A: SECURE-FIT-HOLES.
1111-B: BOTTOM-CAP.
1111-C: SECURE-FIT-HOLES.
1112: FINGER-GUARD.
1112-A: SPACE-INDENTION.
1113: AIR-STREAM-CONE.
1113-A: SCREW-MOUNT.
1113-B: WIRE-PASS-THROUGH.
1113-C: SPACER.
1114: ELECTRIC-TURBINE.
1114-A: SECURE-PADS.
1114-B: SUPPORT-TRUSS.
1114-C: TURBINE-WIRING.
1114-D: TURBINE-FAN-BLADES.
1114-E: TUBINE-AIR-FINS.
1115: SOLUTION-PUMP.
1115-A: MAIN-SOLUTION-LINE.
1115-B FEED-LINE.
1116: BRASS-THREE-WAY-SPLITTER.
1117: CIRCUIT-BOARD/CONTROLLER.
1118: SOLUTION-BOTTLE.
1118-A: MOUNT-GRIP.
1118-B: BOTTLE-TOP.
1118-C: QUICK-RELEASE-BUTTON.
1118-D: QUICK-CONNECT.
1118-E: SOLUTION-LINE.
1118-F: FLUID-PICK-UP.
1118-G: ONE-WAY-VALVE.
1119: BOTTLE-BRACKET.
1119-A: BOTTLE-CONNETION.
1120: HANDLE-GRIP.
1120-A: TRIGGER.
1120-B: AIR-BOOST-BUTTON.
1120-C: RUBBER-GRIP.
1120-D: TRIGGER-ACTUATOR
1120-E: CIRCUIT-BOARD.
1120-F: BATTERY-TERMINAL-ARRAY.
1121: PIKATINNY-RAIL.
1122: SIDE-AIR-VENTS.
1122-A: BOTTOM-AIR-VENTS.
1123: POWER-SWITCH.
1124: GRIP-HANDLE.
1125: BATTERY.
1125-A: QUICK-RELEASE.
1126: TOP-CAP-MOUNT-TABS.
1126-A: BOTTOM-CAP-MOUNT-TABS
1130: TOP-CAP.
1130-A: SPRAY-NOZZLE.
1130-B: SOLUTION-LINE.
1130-C: AIR-VENTS.
1140: ~BOTTOM-CAP.
1140-A: SPRAY-NOZZLE.
1140-B: SOLUTION-LINE.
1140-C: AIR-VENTS.

Figure 11B:
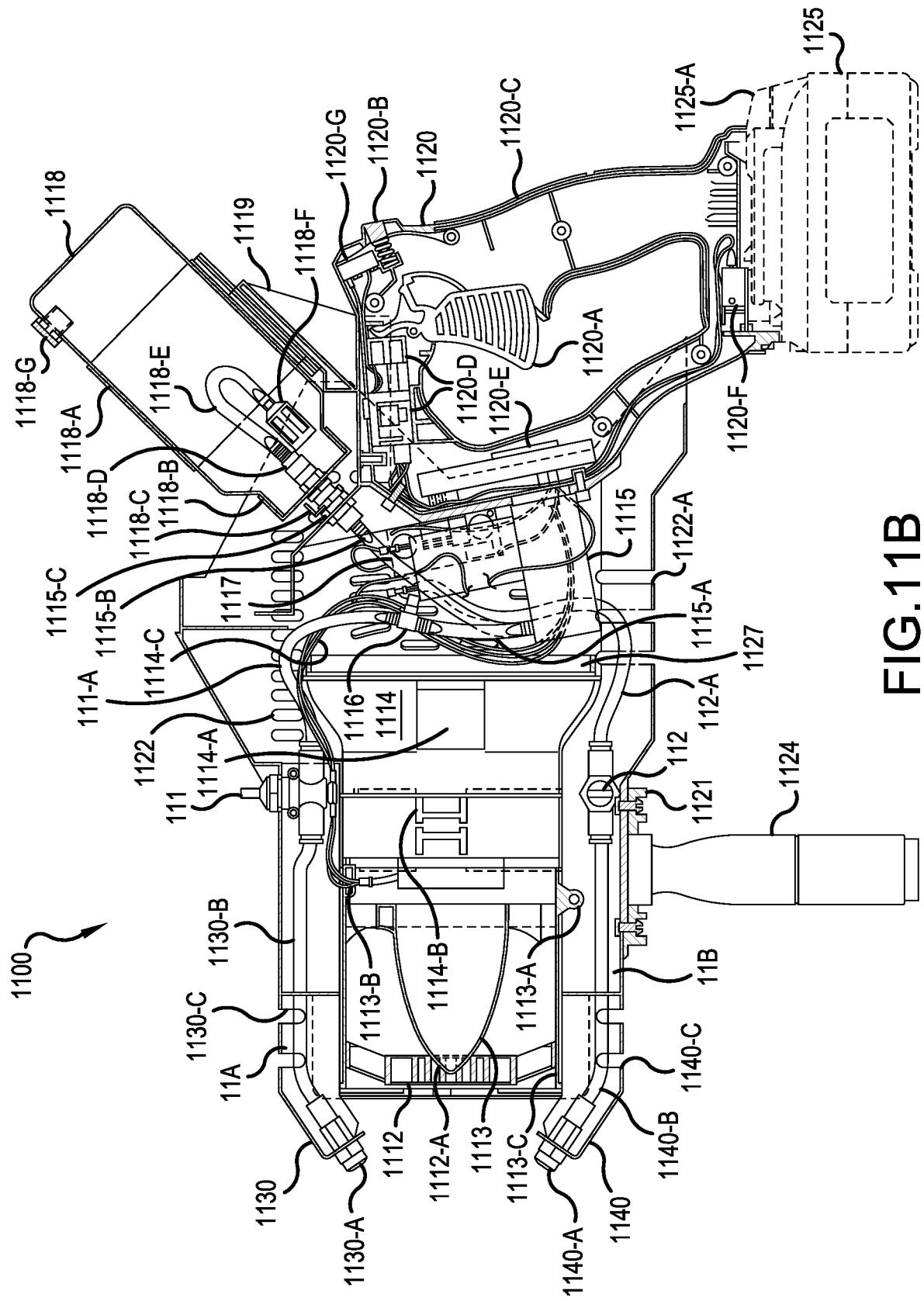
Figure 11C:
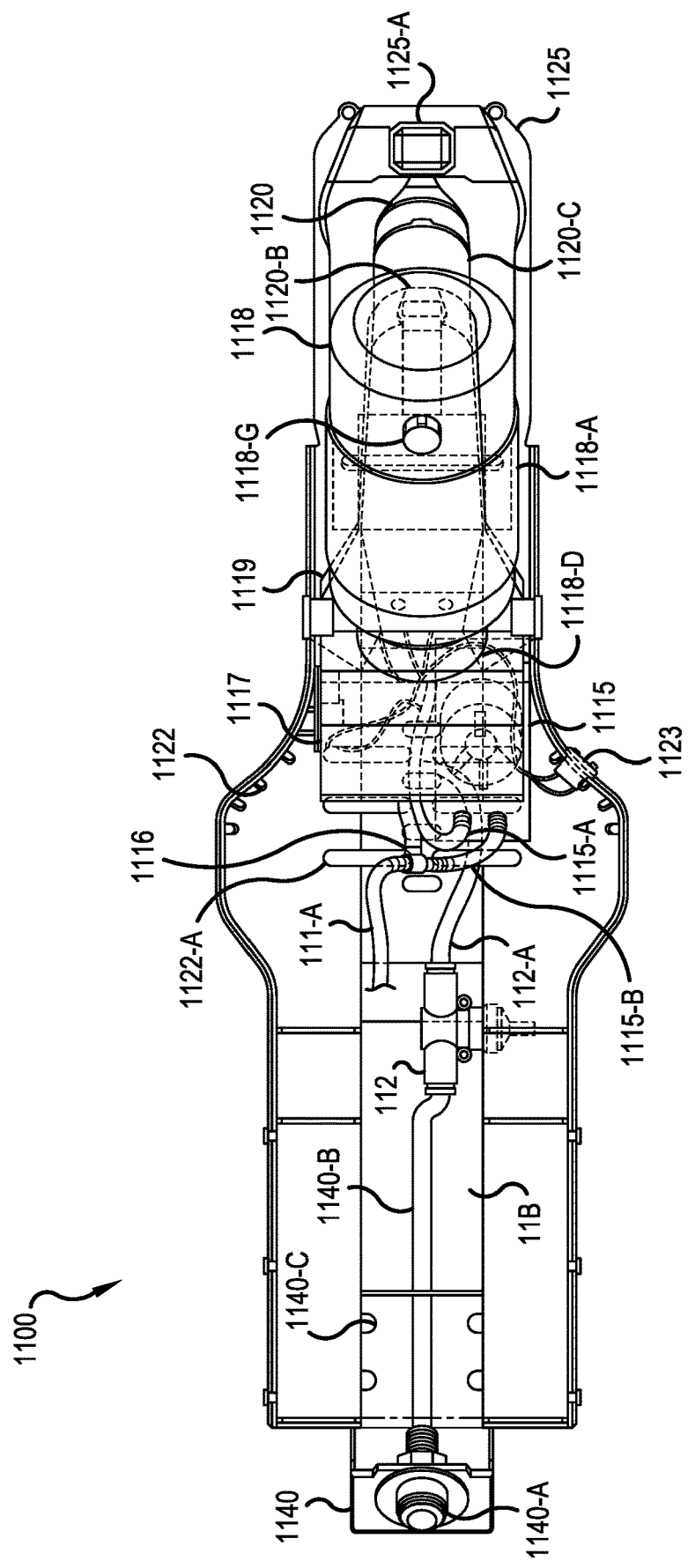
Figure 11D:
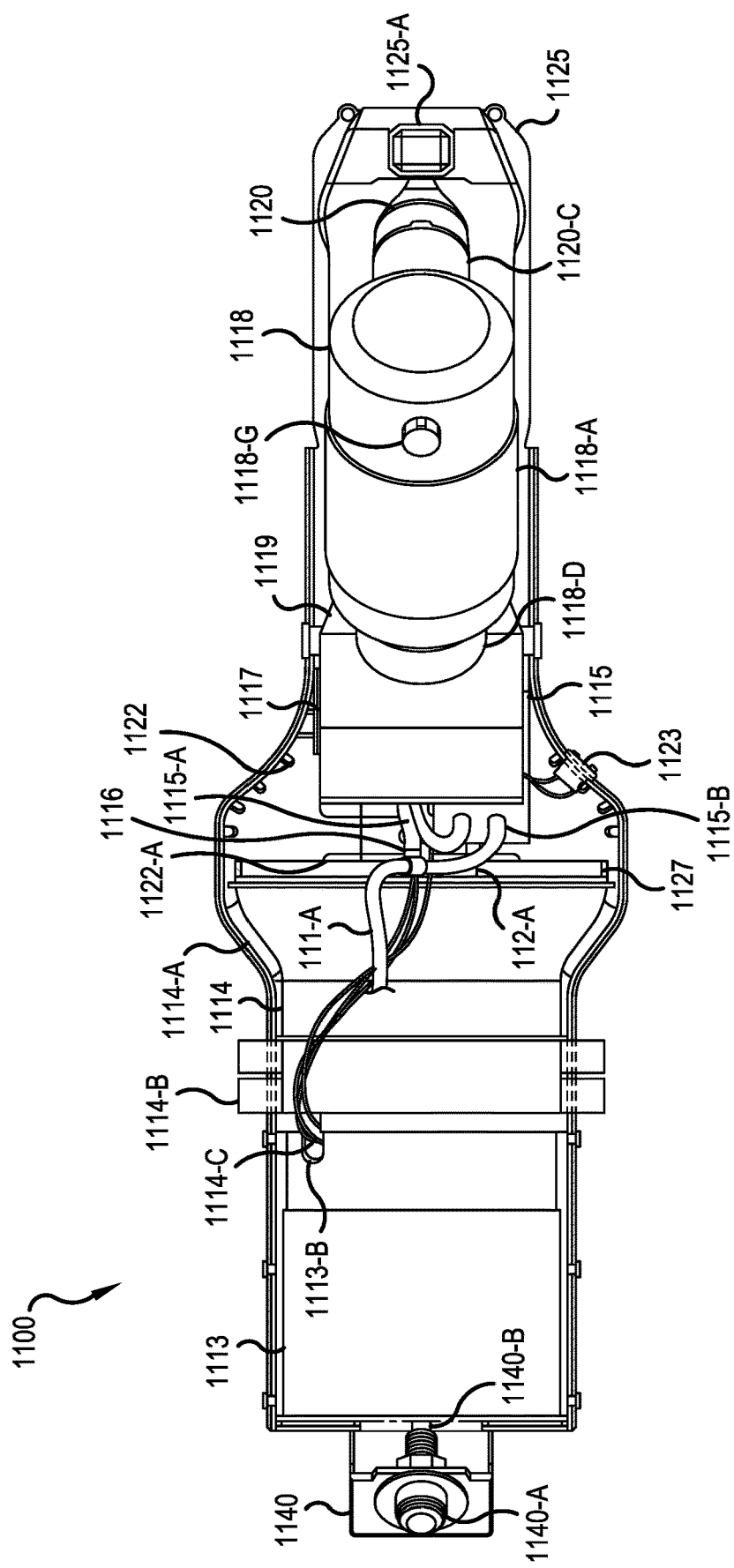
Figure 11E:
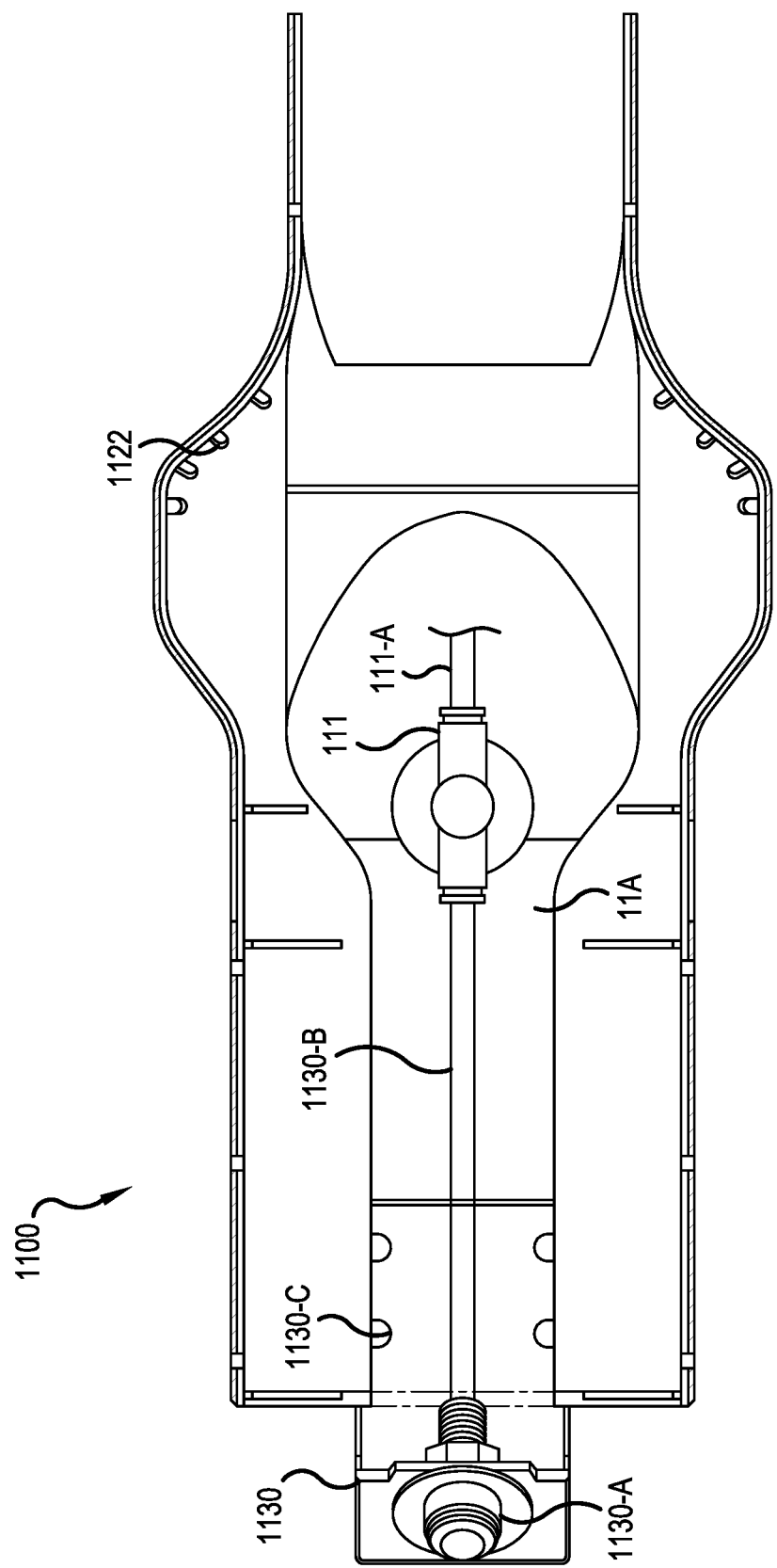

FIG. 11B depicts a cross-sectional view of an exemplary handheld blower device having two spray nozzles 1100 showing the numbered components. FIGS. 11C and 11E depicts a cross-sectional view bottom view of an exemplary handheld blower device having two spray nozzles 1100 showing the numbered components. FIG. 11D depicts a cross-sectional view top view of an exemplary handheld blower device having two spray nozzles 1100 showing the numbered components. In one or more embodiments, the handheld blower device may have one or more spray nozzles. In one or more embodiments either or both of these exemplary handheld blower devices 600 and 1100 may incorporate one or more modular heatable fan blades (100) as disclosed or contemplated herein, and may be used in any method for spraying an area with a solution as disclosed or contemplated herein.

In various implementations, a Tactical Turbine Aerosol Generator™ (T.T.A.G. System™) is a handheld axial air blower capable of dispersing thick vapors of smoke, and filling or covering large and small locations with speed and efficiency. The T.T.A.G-System™ includes a fuel tank which may hold kerosene, a solution pump which siphons the solution from the two solution containers, which feed said solution through a series of solution lines, upon which exit system through a system of spray nozzles by which the atomized liquid communicates with the heat generated by the mini jet turbine, in turn changing the physical state of the atomized liquid into a vapor, and combination of this heat with the vector potential/velocity generated by the mini jet turbine pushes the air in the desired direction.

In various implementations, the Mini-E™ may include the primary function of the T.T.A.G™ in which both share the same or similar base component structures including an axial blower, a pump, a solution bottle, solution lines, and spray nozzles. The primary function is what separates each as a distinct form factor. The T.T.A.G™ is an aerosol generator, however, unlike the Mini-E which coats using liquid base compounds, the T.T.A.G.™ system uses the liquids to generate thick vapors and/or smoke through a heating of those atomized-liquids.

Aero-Sanitization

The Mini-E operates by generating the laminar flow with the axial blower fan and operates in concert with the UV light, as the vents lining the back sides of the units generate a vortex, drawing in the surrounding air and sanitizing the air as it passes through the UV light rays and passes, with the sterilant aerosol flow from the spray nozzles, back into the environment. Both outside air and air being drawn into the unit are sterilized simultaneously.

The vortex operates in tandem with the UV light and pre-treats incoming air as the sterilant solution particulates/aerosol bonds with any viruses/pathogens by its very design before contacting a surface.

In general, all viruses are coated with proteins and contain genetic material which can either be DNA or RNA. Since both nucleic acids have phosphodiester bonds, the genetic material provides a partial negative charge to the virus. The viral nucleic acid genomes are wrapped in proteins that can be neutral, negative, or positive in charge. Therefore, the net charge of a virus depends upon the cumulative charges of the genetic material and the protein.

The electrical "signatures" of the viruses were extrapolated from the results obtained as follows: when the virus particles are more polarizable than the suspension medium, the charge density at the internal aspect of the interface between the particles and the medium is greater than the charge density at the external aspect of the interface. Thus, the net induced dipole on the virus particle is aligned with the applied electric field.

Di polarity or the dipole is a factor in the quantification of a virus. Citing of those facts, use of the electrostatic unit in particular creates a positive/+charge=net-result>virus'−charge-density×EMF=1. In other words, the electrical field generated by the electrostatic unit is exponentially greater of the charge density with the virus, therefore the virus will polarize to match said EMF/electromagnetic field.

Robotic Mounting

In various implementations, an axial blower truss includes a robotic mounting function. Protruding from the left and right-sides of the Mini-E shell are a set of trusses. These trusses may be used along with primary functions of the device and used to facilitate mounting of the device with a robot or some other mobile-platform(s).

Thrust Vectoring

The velocity or air speed may be accomplished according to the disclosure by controlling the magnitude and direction of the airflow. The physical diffuser may be equally controlled and used to direct the airflow. This grants an advantage, whereby the diffuser can be positioned to concentrate airflow in a desired direction, avoiding any need to tilt, turn, or make any adjustments to the unit. This function can be controlled through analog or digital-spurring. In the general-sense, vectoring controls the angle of which the air is flowing from the main stator or axial blower fan through the venturi or shell of the Mini-E, which then contacts with the surface wings or slats of the diffuser, which diverts the air toward the desired direction, e.g., up or down.

System Timer

In various implementations, a system timer is included which functions as a time measurement mechanism and documentation of the operational period with the Mini-E™ This feature mints or documents or records the whole duration of use of the unit, including the operational time and solution use and further, operates as an odometer or meter for the pump component(s), thereby enabling monitoring and maintenance of the longevity and/or warranty of the device component(s).

Tethering Systems and Extended Operation Functions

In various implementations, belt clip solution bottles are included with the variants, of which embodiments include the 1 L through 2 L capacity bottles for the mid-range coatings and are included and secured in place by a nylon jacket. The backpack can manage large range coatings, using the 1-gal capacity of the bottle which may be used for a sterilant.

For the backpack and belt clip solution bottles, each connects to the Mini-E™ by a standard 4 mm line through a quick connection and meter valve is with a 4 mm line of which measures and controls the flow rate of the solution by the belt clip solution bottles and backpack peripherals. The advantages of this tether system include variable positions in which the Mini-E can hold, in particular upside-down, due to the solution containers not needing to be connected to the physical system (e.g., Mini-E).

Flushing Options

Water-Flush: If required to flush system, remove the solution bottle and fill with water, and connect back to unit for flushing.

Air-Flush: By attaching an air hose to the auxiliary valve of the solution pump, air will travel through the solution lines and spray nozzles clearing of any calcification by the sterilant.

Peristaltic Pump

The peristaltic pump creates positive placement or time release of the concentrate through a rotary motion or analog or by a digital signaling of a roller with which contacts with a flexible tube, pinching the tube, creating a meter flow of the concentrate.

Methods of Assembly and Use

SYSTEM POWER ON and COATING MECHANICS of the Mini-E, Mini-E Quad-Flow 600, and Mini-E Dual-Flow 1100:
  1: Connect Battery Pack. Make sure battery is with a good charge before use.
  2: Fill Solution Bottle with the pertinent disinfectant composition.

3: Connect the Solution Bottle to the back of the unit via a Quick Connect/Quick Release system.
4: Select which Spray Nozzle to use by turning either top or bottom Flow Valves. Top is for the light spray and bottom is for a heavy spray. User has the option to combine top and bottom Spray Nozzles in tandem by actuating "ON" both of the Flow Valves.
5: Push the Power Switch. Voice Prompt will activate, "System 'ON'". This activates the Pump. Once the Pump is activated a constant low volume mist of the aerosol will billow from the Spray Nozzles and in tandem power the internal U.V. light.

6: Spurring of the Trigger will start the Axial Blower Fan, pushing the aerosol to the cited location. For the location in which surface(s) are out of the purview of the base max distance of the Axial Blower Fans range an optional Boost Button will increase the fan speed of the Axial Blower Fan.

7: For the coating of the metal surfaces where sterilant needs to bond, activate the switch for the Electrostatic Unit. These will positive charge the sterilant before it exits the Mini E™.

8: Darker locations can be illuminated switching on the L.E.D. Ring Light in front of the unit or Lumens Puck located on the Grip Handle base on the current lighting conditions.

SHUT DOWN MECHANICS of the Mini E™:

9: Once surface(s) have been coated, close Flow Valves, shut down functions by pressing the Power Switch, activating the Voice Prompt, "System "OFF"", and remove the Battery Pack and Solution Bottle.

11: Store in a safe place.

RANGE FUNCTIONS of the Mini E™:

12: For the Mid through the Large range coating jobs, Mini E™ tenders of the two viable peripherals, consisting of a Belt Clip Solution Bottle(s) and/or Backpack:

Belt Clip Solution Bottles are with the variants of which embodiments consisting of the 1 through the 2 Liter capacity for the Mid Range Coatings and are with the secure containment by a Nylon Jacket Whereby the Backpack can manage of the Large Range Coatings, with the 1 Gallon capacity of the disinfectant.

For the Backpack and Belt Clip Solution Bottles, each connects to the Mini E™ by a standard 4 mm line through a quick connection and Meter Valve is with 4 mm line of which measures and controls the flow rate of the solution by the Belt Clip Solution Bottles and Backpack peripherals. For the advantages of this tether system is with the claim of the variable positions in which the Mini E can held, in particular upside down, due to the solution containers not needing to be connected to the physical system/Mini E™.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way appreciably intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications can be referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present disclosure is not entitled to antedate such publication by virtue of prior present disclosure. Further, the dates of publication provided herein can be different from the actual publication dates, which can require independent confirmation.

The patentable scope of the present disclosure is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

Insofar as the description above and the accompanying drawing disclose any additional subject matter that is not within the scope of the claims below, the disclosures are not dedicated to the public and the right to file one or more applications to claims such additional disclosures is reserved.

The foregoing descriptions of specific embodiments of the present invention have been presented for purposes of illustration and description. They are not intended to be exhaustive or to limit the present invention to the precise forms disclosed, and modifications and variations are possible in view of the above teaching. The exemplary embodiment was chosen and described to best explain the principles of the present invention and its practical application, to thereby enable others skilled in the art to best utilize the present invention and its embodiments with modifications as suited to the use contemplated.

It is therefore submitted that the present invention has been shown and described in the most practical and exemplary embodiments. It should be recognized that departures may be made which fall within the scope of the invention. With respect to the description provided herein, it is submitted that the optimal features of the invention include variations in size, materials, shape, form, function and manner of operation, assembly, and use. All structures, functions, and relationships equivalent or essentially equivalent to those disclosed are intended to be encompassed by the present invention.

The following is claimed:

1. A heatable fan blade component for a handheld blower device, the heatable fan blade component comprising:

a fan blade having a resistor puck disposed within a cavity of the fan blade, wherein a current passes through the resistor puck, the resistor puck and the cavity are heated;

wherein the current is deliverable by a power source that is operably connectable to the resistor puck and configurable to deliver the current thereto.

2. The heatable fan blade component of claim 1, wherein the power source includes a brushless direct current (BLDC) motor.

3. The heatable fan blade component of claim 2, wherein the BLDC motor includes a stator and a receiver coil operably connected to the resistor puck, wherein the stator is configured to produce an alternating magnetic field to transfer the current to the receiver coil and the resistor puck.

4. The heatable fan blade component of claim 3, wherein the resistor puck and the cavity are heated by the current and the rotor and the fan blade are rotated, a local air column within the handheld blower device is heated.

5. The heatable fan blade component of claim 1, wherein the fan blade is one of a plurality of fan blades and the resistor puck is one of a plurality of resistor pucks, wherein each resistor puck is disposed within a corresponding fan blade and is operably connectable to the power source to heat the resistor puck and a corresponding cavity of the corresponding fan blade.

6. The heatable fan blade component of claim 5, wherein the plurality of fan blades includes seven fan blades and the plurality of resistor pucks includes seven resistor pucks.

7. A handheld blower device, comprising:
a heatable fan blade component comprising a fan blade having a resistor puck disposed within a cavity of the fan blade, wherein a current passes through the resistor puck, the resistor puck and the cavity are heated; and
a power source operably connected to the resistor puck and configured to deliver the current thereto.

8. The handheld blower device of claim 7, wherein the power source includes a brushless direct current (BLDC) motor.

9. The handheld blower device of claim 8, wherein the BLDC motor includes a stator and a receiver coil operably connected to the resistor puck, wherein the stator is configured to produce an alternating magnetic field to transfer the current to the receiver coil and the resistor puck.

10. The handheld blower device of claim 9, wherein the resistor puck and the cavity are heated by the current and the rotor and the fan blade are rotated, a local air column within the handheld blower device is heated.

11. The handheld blower device of claim 7, wherein the fan blade is one of a plurality of fan blades and the resistor puck is one of a plurality of resistor pucks, wherein each resistor puck is disposed within a corresponding fan blade and is operably connectable to the power source to heat the resistor puck and a corresponding cavity of the corresponding fan blade.

12. The handheld blower device of claim 11, wherein the plurality of fan blades includes seven fan blades and the plurality of resistor pucks includes seven resistor pucks.

13. A method for spraying a solution onto an area with a handheld blower device, the method comprising:
filling a solution bottle of the handheld blower device with the solution;
configuring a spray nozzle of the handheld blower device for use;
activating a pump of the handheld blower device to pump the solution from the solution bottle to the spray nozzle;
actuating a trigger of the handheld blower device to activate an axial blower fan of the handheld blower device; and
directing the spray nozzle of the handheld blower device toward the area to spray the solution from the spray nozzle onto the area;
wherein the handheld blower device comprises:
a heatable fan blade component comprising a fan blade having a resistor puck disposed within a cavity of the fan blade, wherein a current passes through the resistor puck, the resistor puck and the cavity are heated; and
a power source operably connected to the resistor puck and configured to deliver the current thereto.

14. The method of claim 13, wherein the power source includes a brushless direct current (BLDC) motor.

15. The method of claim 14, wherein the BLDC motor includes a stator and a receiver coil operably connected to the resistor puck, wherein the stator is configured to produce an alternating magnetic field to transfer the current to the receiver coil and the resistor puck.

16. The method of claim 15, wherein the resistor puck and the cavity are heated by the current and the rotor and the fan blade are rotated, a local air column within the handheld blower device is heated.

17. The method of claim 13, wherein the fan blade is one of a plurality of fan blades and the resistor puck is one of a plurality of resistor pucks, wherein each resistor puck is disposed within a corresponding fan blade and is operably connectable to the power source to heat the resistor puck and a corresponding cavity of the corresponding fan blade.

18. The method of claim 17, wherein the plurality of fan blades includes seven fan blades and the plurality of resistor pucks includes seven resistor pucks.

19. The handheld blower device of claim 7 wherein the handheld blower device accepts one or more spray nozzles in an assembly of one, two, three, four, or more spray nozzles.

20. The handheld blower device of claim 7 wherein the handheld blower device is a Tactical Turbine Aerosol Generator.

21. The handheld blower device of claim 7, further comprising an aero sanitation component having a UV light configured to sanitize incoming air of pathogens before contacting a surface.

22. The handheld blower device of claim 7, further comprising at least one of: a clipping tethering component, a backpack tethering component, a power component, and a peristaltic pump component.

* * * * *